US007550152B2

(12) United States Patent  (10) Patent No.: US 7,550,152 B2
Pandit et al.  (45) Date of Patent: Jun. 23, 2009

(54) TISSUE GRAFT SCAFFOLD MADE FROM CHOLECYST-DERIVED EXTRACELLULAR MATRIX

(75) Inventors: Abhay Pandit, Galway (IE); Thapasimuthu Vijayamma Anilkumar, Trivandrum (IN)

(73) Assignee: National University of Ireland, Galway, Galway (IE)

( * ) Notice: Subject to any disclaimer, the term of this patent is extended or adjusted under 35 U.S.C. 154(b) by 349 days.

(21) Appl. No.: 11/226,035

(22) Filed: Sep. 14, 2005

(65) Prior Publication Data

US 2006/0159664 A1 Jul. 20, 2006

(30) Foreign Application Priority Data

Jan. 19, 2005 (IE) .................................. 2005/0018

(51) Int. Cl.
*A61F 2/00* (2006.01)
(52) U.S. Cl. ....................................... 424/423; 424/551
(58) Field of Classification Search ....................... None
See application file for complete search history.

(56) References Cited

U.S. PATENT DOCUMENTS

2002/0076816 A1* 6/2002 Dai et al. ..................... 435/455
2002/0094573 A1* 7/2002 Bell ............................. 435/398

OTHER PUBLICATIONS

Schmidt C.E. and Baier J.M. Acellular vascular tissues: natural biomaterials for tissue repair and tissue engineering, Biomaterials, 2000, 21: 2215-2231, entire document.*
Geetha A. Biochemical and physicochemical changes in collagen isolated from the gall bladder of gall stone patients, J. Biochem. Mol. Biol. Biophys., Dec. 2002, 6(6): 421-425, entire document.*
The Term "Derive", Merriam-Webster online dictionary, p. 1, in particular (2008).*
Abrams, et al, "Nanoscale Topography of the Corneal Epithelial Basement Membrane of the Human", *Cornea*, 2000, pp. 57-64, vol. 19, No. 1.
Ando, et al, "Purification and Characteristics of a Novel Transglutaminase Derived from Microorganisms", *Agric. Biol. Chem.*, 1989, pp. 2613-2617, vol. 53, No. 10.
Anilkumar, et al, "Cholecyst derived Extracellular Matrix: A Potential Scaffold", *European Conference on Biomaterials*, Sep. 11-15, 2005, p. 1.
Arokoski, et al "Decreased Birefringence Of The Superficial Zone Collagen Network in the Canine Knee (Stifle) Articular Cartilage After Long Distance Running Training, Detected By Quantitative Polarized Light Microscopy", *Ann. Rheum. Dis.*, 1996, pp. 253-264, vol.
Barbucci, et al, "Micropatterned Surfaces for the Control of Endothelial Cell Behavior" *Biomolecular Engineering*, 2002, pp. 161-170, vol. 19.

Bigi, et al, "X-ray Diffraction and Polarizing Optical Microscopy Investigation of the Structural Organization of Rabbit Tibia", *Journal of Biomedical Materials Research*, 1998, pp. 289-295.
Billiar, et al, "Biaxial Mechanical Properties of the Natural and Glutaraldehyde Treated Aortic Valve Cusp-Part I: Experimental Results", *Journal of Biochemical Engineering*, 2000, pp. 23-30, vol. 122.
Booth, et al "Tissue Engineering of Cardiac Valve Prostheses I: Development and Histological Characterization of an Acellular Porcine Scaffold", *J. Heart Valve Disease*, 2002, pp. 457-462, vol. 11, No. 4.
Braber, et al "Effect of Parallel Surface Microgrooves and Surface Energy on Cell Growth" *Journal of Bio. Mat. Res.*, 1995, pp. 511-518, vol. 29.
Den Braber, et al, "Quantitative Analysis of Cell Proliferation and Orientation on Substrata with Uniform Parallel Surface Micro-Grooves", *Biomaterials*, 1996, pp. 1093-1099, vol. 17, No. 11.
Brody, et al, "Characterizing Nanoscale Topography of the Aortic Heart Valve Basement Membrane for Tissue Engineering Heart Valve Scaffold Design", *Tissue Engineering*, 2006, pp. 413-421, vol. 12, No. 2.
Brody, et al, "Microarchitectural Characterization of the Aortic Heart Valve", *Biomaterials: From Molecules to Engineered Tissues*, N. Hasirci and J.V. Hasirci, Ed., 2004, pp. 167-186.
Choi, et al, "Two-Dimensional Stress-Strain Relationship for Canine Pericardium", *J. of Biomech. Eng.*, 1990, pp. 153-159, vol. 112.
Christie, et al, "Biaxial Mechanical Properties of Explanted Aortic Allograft Leaflets" *Ann. Thorac. Surg.*, 1995, pp. S160-S164, vol. 60.
Christie, et al, "Mechanical Properties of Porcine Pulmonary Valve Leaflets: How Do They Differ From Aortic Leaflets?", *Ann. Thorac. Surg.*, 1995, pp. S195-S199, vol. 60.
Chung, et al, "Enhancement of the Growth of Human Endothelial Cells by Surface Roughness at Nanometer Scale", *Biomaterials*, 2003, pp. 4655-4661, vol. 24.
Curtis, et al "Control of Cell Behavior: Topological Factors", *Journal of the National Cancer Inst.*, 1964, pp. 15-26, vol. 33, No. 1.
Dalby, et al, "Fibroblast Reaction to Island Topography: Changes in Cytoskeleton and Morphology with Time", *Biomaterials*, 2003, pp. 927-935, vol. 24.
Dalby, et al, "In Vitro Reaction of Enothelial Cells to Polymer Demixed Nanotopography", *Biomaterials*, 2002, pp. 2945-2954, vol. 23.
Evans, et al, "Persistent Adhesion of Epithelial Tissue is Sensitive to Polymer Topography", *Journal of Biomedical Materials Research*, 1999, pp. 485-493.
Flemming, et al, "Effects of Synthetic Micro-and Nano-Structured Surfaces on Cell Behavior", *Biomaterials*, 1999, pp. 573-588, vol. 20.
Fratesi, et al, "Effects of Sem Preparation Techniques on the Appearance of Bacteria and Biofilms in the Carter Sandstome", *Journal of Sedimentary Res.*, 2004, pp. 858-867, vol. 74, No. 6.
Freytes, et al, "Biaxial Strength of Multilaminated Extracellular Matrix Scaffolds", *Biomaterials*, 2004, pp. 2353-2361, vol. 25.

(Continued)

*Primary Examiner*—Sandra Saucier
*Assistant Examiner*—Satyendra K Singh
(74) *Attorney, Agent, or Firm*—McDonnell Boehnen Hulbert & Berghoff

(57) ABSTRACT

Bioengineered tissue graft scaffolds and method for producing such scaffolds are provided. The scaffolds are useful to replace or repair damaged mammalian tissues and organs.

9 Claims, 16 Drawing Sheets

OTHER PUBLICATIONS

Fung, "Biomechanics Mechanical Properties of Living Tissues", 2nd Edition, *New York: Springer-Verlag*, 1993, pp. vii-568.

Gloeckner, et al, "Mechanical Evalution and Design of a Multilayered Collagenous Repair Biomaterial", *Journal of Biomedical Materials Research*, 2000, pp. 365-373.

Gu, et al, "Action of Protein-Glutaminase on α-Lactalbumin in the Native and Molten Globule States", *J. Agric. Food Chem.*, 2001, pp. 5999-6005, vol. 49, No. 12.

Hiester, et al, "Optimal bovine pericardial tissue selection sites. I. Fiber architecture and tissue thickness measurements*", *Journal of Biomedical Materials Research*, 1998, pp. 207-214.

Ikura, et al, "Crosslinking of Soybean 7S and 11S Proteins by Transglutaminase*", *Agric. Biol. Chem*, 1980, pp. 2979-2984, vol. 44, No. 12.

Jacques, et al "Imaging Superficial Tissues with Polarized Light", *Lasers in Surgery and Medicine*, 2000, pp. 119-129, vol. 26.

Jearanaikoon, et al, "An X-ray microscopy perspective on the effect of glutaraldehyde fixation on cells", *Journal of Microscopy*, 2005, pp. 185-192, vol. 218 (Part II).

Kang, et al, "Effect of Disulfide Bond Reduction on Bovine Serum Albumin-Stabilized Emulsion Gel Formed by Microbial Transglutaminase", *Journal of Food Science*, 2003, pp. 2215-2220, vol. 68. No. 7.

Karuri, et al, "Biological Length Scale Topography Enhances Cell-Substratum Adhesion of Human Corneal Epithelial Cells", *Journal of Cell Science*, 2004, pp. 3153-3164, vol. 117, No. 15.

Kurth, et al, "Transglutaminase Catalyzed Cross-Linking of Myosin to Soya Protein Casein and Gluten", *Journal of Food and Science*, 1984, pp. 573-576, vol. 49.

Lu, et al, "Novel Porous Aortic Elastin and Collagen Scaffolds for Tissue Engineering", *Biomaterials*, 2004, pp. 5227-5237, vol. 25.

Meyle, et al, "Variation in Contact Guidance By Human Cells on a Microstructured Surface", *Journal of Biomedical Materials Res.*, 1995, pp. 81-88, vol. 29.

Motoki, et al, "Crosslinking Between Different Food Proteins by Transglutaminase", *Journal of Food Science*, 1983, pp. 561-566, vol. 48.

Murphy, et al, "Substratum Topography Modulates Proliferation of Corneal Epithelial Cells", *Invest. Ophthalmol. Vis. Sci*, 2004, p. E-Abstract 3817-B278, vol. 45.

Peters, et al "Effects of Nano-Scaled Particles on Endothelial Cell Function in Vitro: Studies on Viability, Proliferation and Inflammation", *Journal of Materials Science: Materials in Medicine*, 2004, pp. 321-325, vol. 15.

Sacks, et al, "Quantification of The Fiber Architecture and Biaxial Mechanical Behavior of Porcine Intestinal Submucosa", *Journal of Biomedical Materials Research*, 1998, pp. 1-10.

Steinhoff, et al, "Tissue Engineering of Pulmonary Heart Valves on Allogenic Acellular Matrix Conduits", *Circulation*, 2000, pp. III-50-III-55, vol. 102 (Supp. III).

Teixeira, et al "Epithelial Contact Guidance on Well-Defined Micro- and Nanostructured Substraytes", *Journal of Cell Science*, 2003, pp. 1881-1892, vol. 116, No. 10.

Thubrikar, et al, "The Arotic Valve", *CRC Press Inc.* Boca Raton, Florida, pp. 1-221, (1990).

Van Wachem, et al, "In vivo biocompatibility of carbodiimide-crosslinked collagen matrices", *Journal of Biomedical Materials Research*, 2000, pp. 368-378.

* cited by examiner

A B

A B

TISSUE GRAFT SCAFFOLD MADE FROM CHOLECYST-DERIVED EXTRACELLULAR MATRIX

FIELD OF THE INVENTION

The present invention relates to bioengineered tissue graft scaffolds and to methods of producing such scaffolds. The scaffolds find uses to replace or repair damaged mammalian tissues and organs.

In this context a scaffold can be defined as a biodegradable material that supports the growth of cells and will eventually degrade leaving behind regenerated tissue structure. The scaffold provides a support upon which cells can organise and develop.

BACKGROUND OF THE INVENTION

Tissue engineering attempts to create three-dimensional tissue structures on which cells and other biomolecules may be incorporated. These structures or scaffolds guide the organization, growth and differentiation of cells in the process of forming functional tissue by providing physico-chemical cues. To successfully incorporate a scaffold within the host body depends on efficient communication between cells, tissues and the host system as a whole. The scaffolds and cells to be incorporated must interact with adhesion and growth factor receptors and the scaffold must eventually degrade.

Many disease conditions or injuries of the body require the repair or replacement of damaged tissues, but the body itself may not be able to replace or repair the tissue satisfactorily or within an appropriate time scale. Thus many methods of disease or injury treatment involve methods of augmenting the body's natural repair mechanisms and often rely on the use of implantable biological scaffolds or prostheses. Ideally an implantable prosthesis should be chemically inert, noncarcinogenic, capable of resisting mechanical stress, sterilisable and resistant to the actions of tissue fluids as well as being non-inflammatory and hypoallergenic.

A number of scaffolds are known. These scaffolds may be synthetic and/or biological in nature.

Biological scaffolds have a number of advantages in that communication with existing body cells is instantaneous, they undergo a natural process of degradation, and existing biological signals attenuate incorporated signals such as the growth factors and cytokines which are inherently present in these scaffolds. On the other hand, these scaffolds exhibit great variability in terms of their morphological and biological properties, they are complex to manufacture and susceptible to contamination. Additionally, modifications are not as easy compared to synthetic scaffolds. There are limitations such as size, shape and the properties that can be imparted to a biological scaffold. Biological scaffolds are subjected to a number of processing procedures such as sterilizing and cross-linking before implantation. These processing procedures may alter the innate characteristics of the scaffold. The best processing procedure will minimize the loss of natural scaffold-properties. Thus the minimally altered scaffold will retain most natural molecules required to establish the expected therapeutic properties of the tissue-engineered organ or tissue. Upon implantation, these retained natural molecules are also further amenable to natural degradation. The biomolecular architecture of a biological scaffold might not have been extensively studied and documented poorly compared to synthetic scaffolds. This ignorance is very often acceptable so long as the isolated scaffold continues to provide favourable or desired function over detrimental effects.

Synthetic scaffolds have the disadvantage that cell recognition is difficult, surface alterations such as mobilisation of growth factors to the scaffold (to permit cell migration, proliferation and adhesion) might be needed in some applications, they are subject to hydrolysis/enzymatic degradation and generate no biological signals. On the other hand they are consistent, easy to manufacture, easy to modify, and prototyping is easy.

One of the aims of tissue engineering is the production of tissue construct that can restore or repair lesions to a physiological status compatible with life. Identification of substrates, generally called scaffolds, for supporting growth and function of cells is therefore essential to successful tissue engineering. Various tissues and tissue components of animal origin are currently used as scaffolds. Xenogenic scaffolds have variable properties and still require optimisation of those properties before clinical use. The scaffolds derived from organs like small intestine, urinary bladder and oesophagus of pig, dog and sheep are available for clinical use as for example vascular grafts and skin grafts. However, the search for better scaffold substrates for tissue engineering applications is continuing. Although scaffolds derived from small intestine and urinary bladder can be used for certain applications, they are not suitable for universal use because of their defined range of mechanical and biological properties. Therefore there is continuing need to produce new scaffolds for specific clinical applications.

The present invention in one aspect utilizes transglutaminase in the production of a tissue scaffold. Transglutaminases are a class of natural enzymes that catalyse the acyl-transfer reaction between the ε-amino group of lysine and the γ-carboxyamide group of glutamine in proteins. Recent interest in transglutaminase can be attributed to the discovery of microbial transglutaminase (mTGase), (38) derived from a variant of *Streptoverticillium mobaraense*. mTGase is a calcium-independent enzyme that catalyses the formation of covalent crosslinks between glutamine and lysine residues in proteins. This enzyme has shown promise as a cross-linking agent (36-39) and has a wide range of applications, particularly in the food industry. The effective cross-linking of proteins by mTGase depends not solely on the presence of glutamine and lysine residues in the primary structure but also on the tertiary structure of the protein (40, 41).

In 1964 Curtis et al (2) proposed the concept that cells reacted to the topography upon which they were cultured, since then the study of cellular response to micro-topography has been substantial (3-8) and more recently cellular responses to nano-topography has also been investigated (9-13). Nano-scale topographic features modulate cell adhesion, spreading, focal adhesion formation, orientation, proliferation, differentiation and migration and are thought to have a more substantial influence on cellular behaviour than micro-scale features (10, 13-15). Cells evidently respond to topographical cues and are more likely to form a confluent, fully functional, physiologically similar layer on a topography with which they are familiar.

Several artificial and biological, biodegradable and non-biodegradable tissue engineering products are available to treat a range of tissues and locations throughout the body. Non-biodegradable membranes are prone to rejection in the short term and failure in the long term. Biodegradable membranes have been successful in eliciting a regeneration of body tissue that takes over from the implant as it dissolves. This healed area may be very different from the original tissue, because the prosthetic membrane does not elicit a proper healing response. Natural, acellular materials are being developed to in addition to current technologies to create a biological biodegradable scaffold. The primary structural material for these matrices is collagen but, because they are extracted directly from whole tissue, the signal pathways, enzymes, and growth factors naturally present in these tissues are still present. This sparks a natural healing response in the host tissue. Areas repaired with these materials tend to look and behave more like the original host tissue than ingrowth into inert biodegradable matrices.

Extracellular matrix (ECM) is the natural scaffold responsible for active tissue remodeling—in situ. Submucosa of hollow organs are connective tissues rich in ECM and have minimal cell content. Small intestinal submucosa (SIS) and urinary bladder submucosa are examples of such materials, which have been used as tissue engineering scaffolds with reasonable success.

As used herein the terms 'extracellular matrix' (ECM) is synonymous with the term 'cholecyst-derived extracellular matrix' (CEM) and similarly, ECM as used herein is defined as a tissue derived from the submucosal area of the cholecyst, except where the meaning(s) clearly refers to the extracellular matrix or ECM derived from a different tissue (for example, small intestine). In addition, the term 'gallbladder' is used synonymously with 'cholecyst'.

OBJECT OF THE INVENTION

One object of the present invention is to provide an alternative tissue scaffold. A further object is to provide a tissue scaffold that has a reduced likelihood of inducing an inflammatory response on implantation in a patient. It is also an object to provide a tissue scaffold that harbors fewer cellular remnants than currently available tissue scaffolds. Another object is to provide a tissue scaffold with improved tensile strength. A still further object is to provide an improved method of producing a tissue scaffold.

SUMMARY OF THE INVENTION

The present invention provides a tissue scaffold comprising a sterilised layer or layers of extracellular matrix tissue from the cholecyst (cholecyst). The cholecyst may be of mammalian origin. In further embodiments, the cholecyst may be selected from the group consisting of porcine, bovine, ovine, canine, murine, simian, caprine, equine, avian, leporine and human. Ideally, the cholecyst is porcine. In alternative embodiments, the cholecyst is human. In some embodiment, the cholecyst is human tissue from the patient. In alternative embodiments, the human tissue may be from a separate donor.

The tissue may be cross-linked or fixed. The fixation or cross-linking may be achieved by a method selected from enzymatic cross-linking, glycation, or fixation with formaldehyde, glutaraldehyde, dialdehyde starch, glyceraldehydes, cyanamide, diimides, diisocyanates, dimethyl adipimidate, carbodiimide, epoxy compounds or genepin.

In one embodiment the enzyme used for cross-linking may be a lysyl oxidase or a transglutaminase. A suitable transglutaminase is a tissue transglutaminase derived from pig's liver or a microbial (mTGase) derived from a variant of *Streptoverticillium mobaraense*. The tissue may be cross-linked with a 0.005-0.05% w/v solution of mTGase with an activity of 27000 nmol putrescene incorporated/mg/hour. Preferably a 0.001-0.03% w/v solution is used.

In an alternative embodiment the sugar used for glycation may be a ribose.

In a still further embodiment the tissue may be cross linked by Carbodiimide treatment. Suitably the tissue is treated with 20 mM EDC (1-ethy-3-3-dimethylaminoprpyl carbodiimide-HCl) and 10 mM N-hydroxysuccinimide in Hepes buffer, pH 6.5 for about 72 h.

Suitably the tissue can be made into a composite via creating mechanical composites. The composite may be prepared by alternate stacking of layers of the substrate on top of each other. Depending on the orientation of collagen fibers a range of mechanical properties can thus be attained.

The tissue may be sterilized by a method selected from antibiotic treatment, treatment with peracetic acid or any weak acid or alkali, gamma radiation, or treatment with 60-80% alcohol.

Preferably the cholecyst is porcine or a cholecyst of mammalian origin. The tissue scaffold may be formed into a sheet, a cylindrical tube, a dome or fundus. A foam-based structure may also be made by combining the tissue with other biological structural proteins such as collagen (elastin, etc.) and freeze drying.

The tissue scaffold may be stored for use in a freeze dried state. Alternatively the scaffold may be stored in peracetic acid, gluteraladehyde solution, antimicrobial solution, or frozen, air dried or irradiated for storage or stored in an air-tight container.

The invention also provides a method of producing a tissue scaffold comprising
(a) isolation of the cholecyst,
(b) isolation of the extracellular matrix of the cholecyst,
(c) cleaning and disinfection of the extracellular matrix.

The tissue is preferably disinfected by treatment with at least one antibiotic. The antibiotic may be penicillin or streptomycin or a mixture of the two.

Ethanol is preferably used to clean the tissue. The cleaning step suitably comprises treatment of the tissue with 70% ethanol for at least 2 hours and preferably at least 4 hours.

The method may further comprise the step of decellularisation. Decellularisation may comprise treatment with SDS and trypsin digestion. The tissue may be treated with 1% SDS in 10 mm tries buffer for at least 24 hours, preferably 96 hours. The tissue may then be treated with 0.05% trypsin in 10 mm Tris buffer and 0.1% ETDA pH 8 for at least 12 hours.

Preferably, the tissue is fixed or cross-linked by a method selected from formaldehyde fixation, glutaraldehyde fixation, enzymatic cross-linking, dialdehyde starch fixation, glyceraldehyde fixation, cyanamide fixation, diimide fixation, diisocyanate fixation, dimethyl adipimidate fixation, carbodiimide fixation, fixation with an epoxy compound, genepin crosslinking or glycation.

Suitably the tissue is delaminated. Delamination may be achieved by mechanical means, such as by scraping. Preferably, the tissue is immersed in 10% neutral buffered formalin for at least 1 min and up to 12 hours prior to delamination. Preferably the immersion is for 2-4 hours. This helps to prevent tearing during delamination.

In one embodiment the tissue may be cross-linked using a lysyl oxidase or a transglutaminase. A suitable transglutaminase is a tissue transglutaminase derived from pig's liver or a microbial (mTGase) derived from a variant of *Streptoverticillium mobaraense*.

The tissue may be cross-linked with a 0.005-0.05% w/v solution of mTGase with an activity of 27000 nmol putrescene incorporated/mg/hour. Preferably a 0.001-0.03% w/v solution is used.

In an alternative embodiment the sugar used for glycation may be a ribose.

The tissue scaffold of the present invention has many advantages over the currently available small intestine submucosal tissue scaffold (SIS). SIS is derived from small intestine, which naturally harbours microorganisms, whereas the scaffold of the present invention is derived from cholecyst which is located in the peritoneal cavity and which is sterile. For these reasons it is difficult to ensure aseptic conditions when isolating SIS whereas routine sterile precautions are sufficient for ensuring sterility when isolating the scaffold of the present invention. For-this reason extensive cleaning and sterilisation are essential in the preparation of SIS and this might alter material characteristics of the scaffold. With the present invention there is lesser possibility of alteration of those characteristics because cholecyst extracellular matrix requires minimum cleaning, which essentially results in minimal alterations in the 3D organization of the ECM as well as minimal component leaching.

Furthermore the submucosa of the small intestine is highly cellular due to the nature fibroblasts and submucosal glands, whereas the extracellular matrix of the cholecyst has relatively few cellular components, esp. devoid of vasculature, submucosal glands, lymphatic and nervous networks. Cellular components have been shown to generate antigenicity in the scaffold rendering it to be ineffective in long term applications because of the potential immunogenicity. The scaffold of the present invention is about 130 μm giving the scaffold a more elastic nature. Additionally the proportion of collagen in SIS is less than that in the cholecyst extracellular matrix which means the scaffold of the present invention is stronger.

Acellular matrices offer the field of tissue engineering scaffold design the potential to effectively repair and regenerate structurally complex tissues and organs in a more biomimetic manner than currently available synthetic materials; however, the search for optimal acellular materials is ongoing. The present invention has identified cholecyst-derived extracellular matrix (CEM) as a potentially suitable acellular matrix partly due to its high collagen and low cell contents. Prospective applications of this novel tissue engineering scaffold material include soft tissue augmentations like thoracic wall repair dermal wound healing and abdominal wall reconstruction. Other tissue engineering examples include that of cardiovascular tissue engineering (heart valve, cardiac patches).

Surface topography is a critical parameter in architecturally characterising CEM and subsequently in assessing its suitability as a tissue engineering scaffold. Collagen fibres are the principal structural component of soft and hard biological tissues; they are the load carrying element in blood vessels, skin, tendons, heart valves, cornea, dura mater and bone. The orientation of collagen fibres is intrinsically related to mechanical properties and organ function; tendons and ligaments transmit tension in 1-dimension thus collagen fibres are oriented in 1-dimension, parallel to the transmitted force, collagen orientation in skin is primarily parallel to the surface and collagen orientation is 2-dimensional reflecting more complex loading conditions and collagen orientation in blood vessels and intestinal mucosa is considered most complex (16). Identification of collagen fibre orientation in CEM will not only further characterise the material but will permit the identification of the directions of maximum and minimum mechanical axis and subsequently potential applications for tissue engineering scaffold design. Biaxial mechanical tests are a more easily interpreted and physiologically relevant method of mechanically testing biomaterials when compared to uniaxial and ball burst tests (17). By carrying out biaxial tests on CEM along the principal collagen fibre axis mechanical properties along this axis may be elucidated and compared the properties along the perpendicular axis.

The present invention additionally has characterized the micro-scale and nano-scale architecture of CEM through scanning electron microscopy and polarised ligh. Mechanical response of the material to biaxial loading along the axis of preferred collagen fiber orientation has provided an indication of the behaviour of the material in vivo.

DETAILED DESCRIPTION OF THE INVENTION

Materials and Methods

Isolation of Cholecyst Extracellular Matrix

Cholecyst and small intestine tissue was obtained from market weight pigs, slaughtered at Duffy's Meats abattoir, Gort. Co. Galway. Porcine specimens were fixed immediately post mortem by total immersion in 10% neutral buffered formalin (NBF) for light microscopy and 3% Glutaraldehyde Fixative for electron microscopy. Whole cholecysts were punctured and drained of bile before immersion in fixatives, while small intestinal samples were cut into approximately 10 cm long sections before immersion in fixative. Samples were subsequently transported to a suitable laboratory environment for further tissue processing. Before fixation had fully occurred (2 hours), samples were further processed to allow for total fixation and for the isolation of extra cellular matrix. This process resulted in the procurement of whole tissue and delaminated extra cellular matrix, for light and electron microscopy. Before delamination occurred whole samples were take for analysis, and thickness measurement were taken via an AP-6500 Micrometer screw gauge.

Step 1

Figure 1:
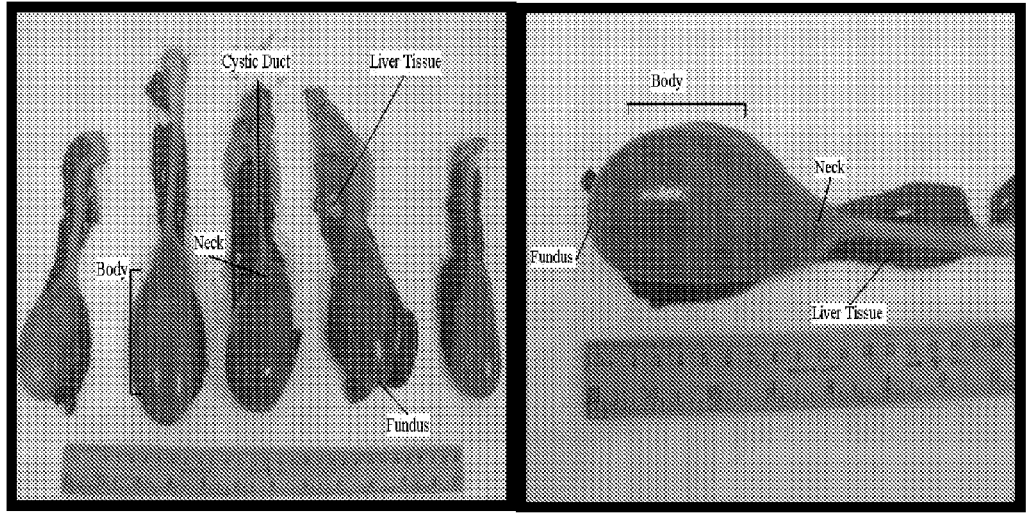
FIG. 1: Isolated porcine cholecyst.
Figure 2:
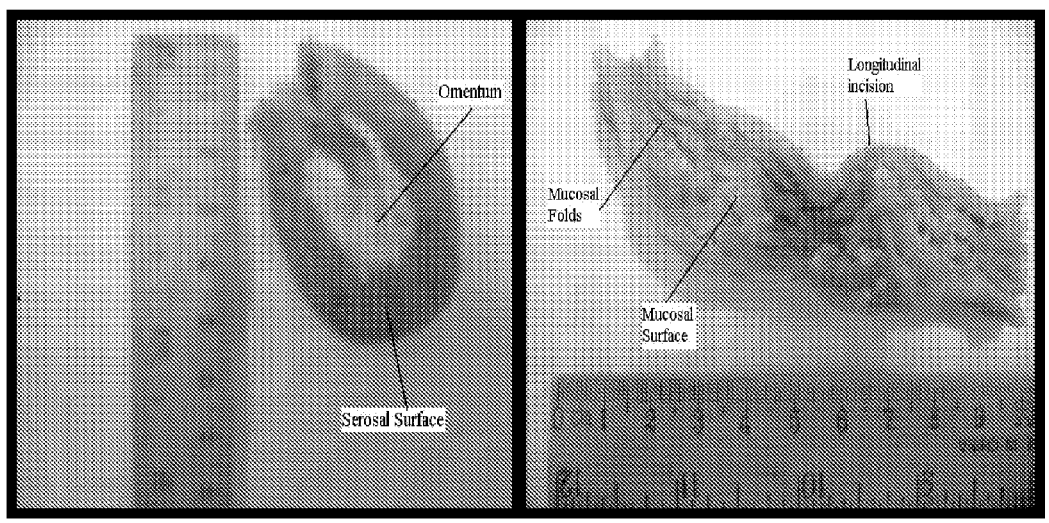
FIG. 2: Isolated porcine small intestine.

Cholecyst and small intestine were removed from the pig gut. Cholecysts were excised from the liver leaving the cystic duct intact. Liver tissue was still connected to the cholecyst following excision and the cholecyst wall was distended with bile (see FIG. 1). Cholecysts measured approximately 10 cm from fundus to neck. 10 cm segments of small intestine was isolated from the pig jejunum and excised from the adjoining omentum (FIG. 2). It was subsequently opened with a longitudinal incision to reveal the inner mucosal surface (see FIG. 2).

Step 2

Figure 3:
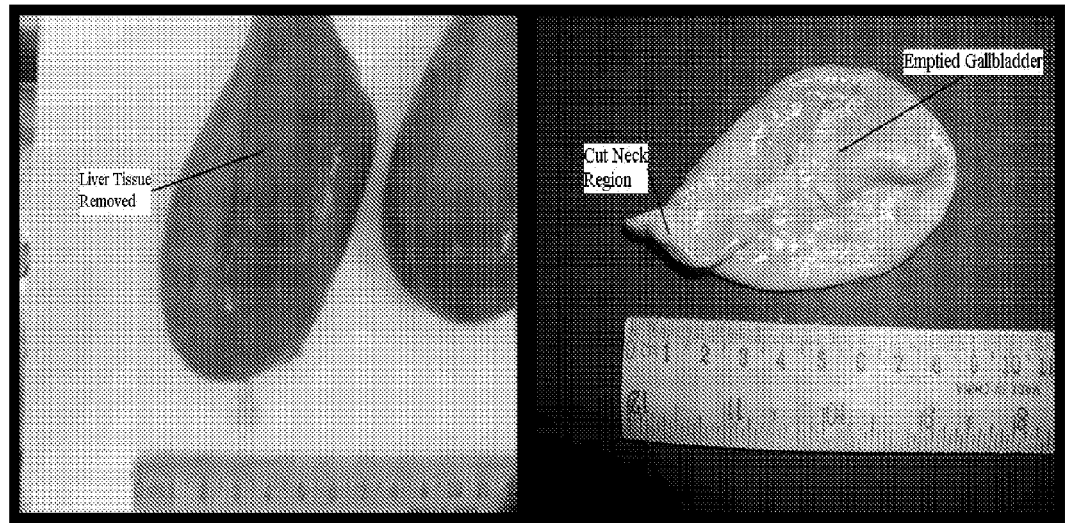
FIG. 3: Cholecyst trimmed of liver tissue (A) and puncture to drain bile (B).
Figure 4:
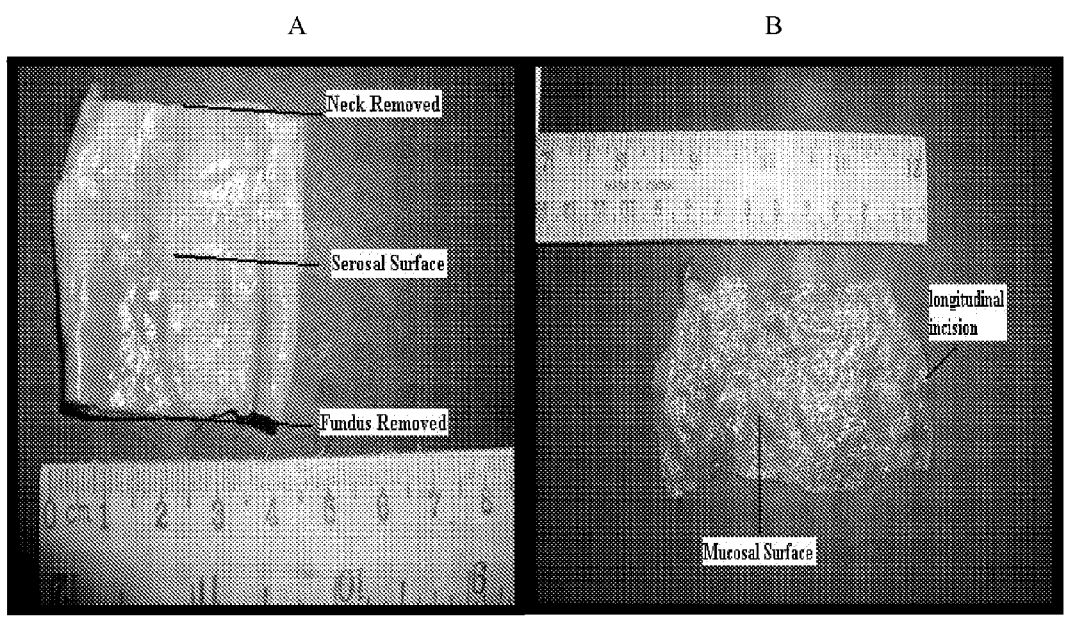
FIG. 4: Cholecyst neck and fungus region removed (A) Mucosal surface revealed by longitudinal incision (B).

Liver tissue was trimmed away from the cholecyst and the cystic duct removed to allow the bile to drain through the neck from the cholecyst lumen (FIG. 3). The fundus and neck regions were subsequently removed (FIG. 4) and the tissue opened via a longitudinal incision to reveal the mucosal surface (FIG. 4)

Step 3

The mucosa and lamina propria, the luminal surface layers were removed as a single entity using a pair of forceps. Cholecyst, although derived from the embryonic foregut tube, lacks muscularis mucosae or submucosa. Below the mucosa and lamina propria is the muscularis layer. This layer was removed by mechanical delamination, using the blunt handle of a scalpel; scraping the tissue in one direction. Similar delaminarion procedure for scraping was also applied to remove the mucosa and lamina propria of the intestinal.

Step 4

The serosal and adipose tissue layers on the outer side of CEM and SIS were removed from the cholecyst and small intestine. These were removed as a single layer using a forceps. For the removal of these layers from the small intestine it was necessary to first immerse the tissue in 10% neutral buffered formalin for I minute to prevent repeated tearing during delamination.

Step 5

Figure 5:
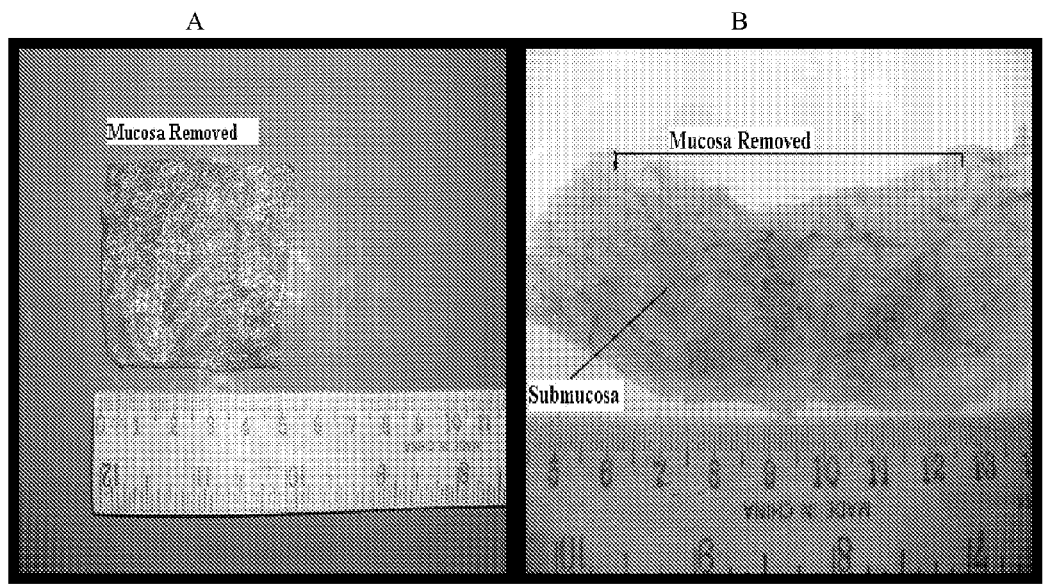
FIG. 5: Mucosal surface delaminated from cholecyst (A) and small intestine (B).
Figure 6:
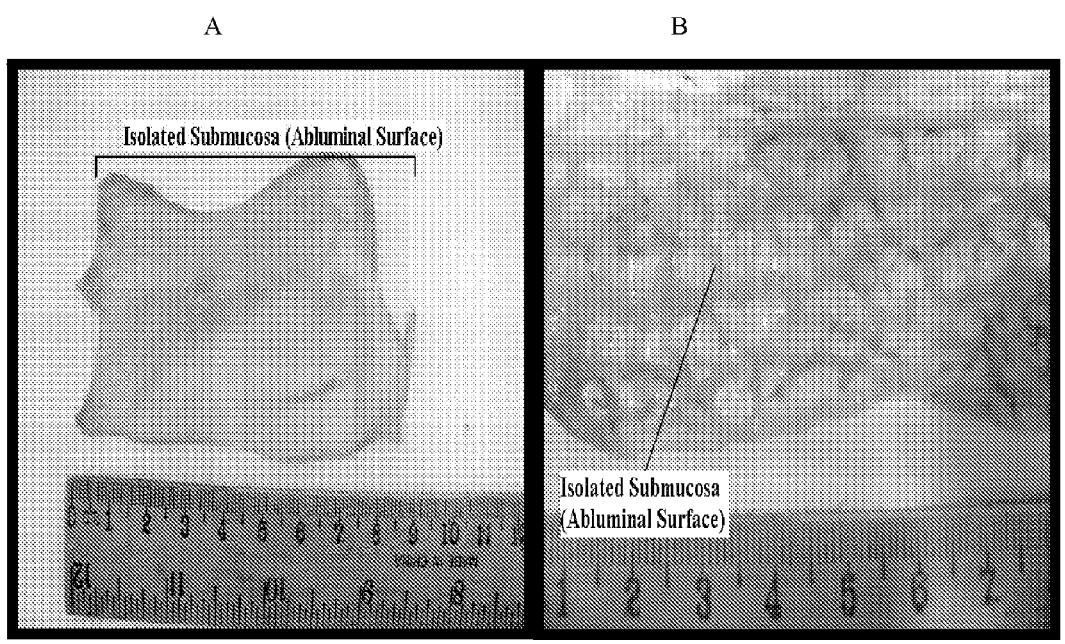
FIG. 6: Isolated cholecyst extracellular matrix (A) and isolated small intestine submucosa (B).

Samples obtained from the cholecyst and intestine submucosa (FIG. 5) were cut into pieces approximately 1.5 $cm^2$, these were fixed overnight in 10% NBF for light microscopy and overnight in 3% Glutaraldehyde Fixative for electron microscopy. Exactly the same procedure fixing was carried out for the laminated cholecyst and small intestine samples.

Specimen Processing for Light Microscopy

Following 24-48 hour fixation in 10% NBF all samples intended for light microscopy were placed in distilled water and prepared for paraffin embedding, However, samples to be stained with toluidine blue were processed according to the procedures used for transmission electron microscopy. Two methods of paraffin wax embedding were investigated:
 1. Samples were dehydrated and infiltrated with paraffin via an automated processing microwave—Micromed T/T Mega microwave processing lab station
 2. Samples were dehydrated in graded alcohols and infiltrated with paraffin by hand.

Microwave Processing:

Samples were placed in polymer cassettes measuring approx. 3 cm×2 cm. These were housed in a cylinder provided with the processing oven and immersed in a dehydrating fluid supplied with the machine—J.F.C. Solution in a 2.5 litre bottle (available from Hacker Instruments). Samples were processed in this solution for approx 40 minutes at 72° C. Samples were then removed from the fluid and immersed in molten paraffin wax for a further 30 minutes at 72° C.

Hand Processing:

Samples were rinsed 3× phosphate buffered saline (PBS), then passed through a series of graded alcohols: PBS is not essential, as distilled water or even tap water may also be used.
 30% ethanol/distilled water solution for 45 minutes;
 50% ethanoldistilled water solution for 45 minutes;
 70% ethanol/distilled water solution for 45 minutes;
 90% ethanol/distilled water solution for 45 minutes;
 100% ethanol for 45 minutes.

Samples were then placed in cassettes and immersed in xylene 3×7 minutes and then immersed in molten paraffin wax for 45 minutes.

Microwave processed and hand processed samples were then placed in individual steel moulds and subsequently set in paraffin wax blocks overnight at 4° C.

Paraffin embedded sections were cut on a HM 200 Ergostar microtome and placed on glass slides in a 37° C. incubator overnight.

Specimen Staining for Light Microscopy

Simple staining was performed to elucidate the structure of both laminated and delaminated cholecyst and small intestine. This procedure involved the use of:
 Haematoxylin and Eosin staining; van Gieson staining and Toluidine blue staining.
 Fluorescent staining was also employed for the unambiguous labelling of cell nuclei.
 All paraffin wax sections were 5 µm in thickness.

Haematoxylin and Eosin

Slides were passed through xylene 2×7 minutes then through a series of graded alcohols for rehydration:
 100% 5 minutes;
 70% 5 minutes;
 50% 5 minutes;

Distilled water for 5 minutes.

Slides were next immersed in Mayer's haematoxylin for 5 minutes, running tap water for 2 minutes then dipped once very quickly in acid alcohol before being returned to running water for 1 minute. Slides were then immersed in eosin for 1 min, tap water for 30 seconds and then blotted dry. Slides were then immersed in xylene for 2 minutes and a drop of DPX mounting media applied to the slide before cover slipping.

Van Gieson

Slides were passed through xylene 2×7 minutes then through a series of graded alcohols for rehydration:
- 100% 5 minutes;
- 70% 5 minutes;
- 50% 5 minutes;
- Distilled water for 5 minutes.

Slides were next immersed in celestine blue for 7 minutes, and then in running tap water for 2 minutes. Slides were next immersed in Mayer's haematoxylin for 5 minutes, running tap water for 2 minutes then dipped once very quickly in acid alcohol before being returned to running water for 1 minute. Slides are then immersed in van Gieson's stain for 1.5 minutes, tap water for 30 seconds and then blotted dry. Slides were then immersed in xylene for 2 minutes and a drop of DPX mounting media applied to the slide before cover slipping.

Toluidine Blue

Samples to be stained with toluidine blue were embedded in a polymer resin and mounted on glass slides after sections I m were cut on an ultramicrotome (see tissue processing for transmission electron microscopy). The toluidine blue stain consisted of a 1% Toluidine blue powder in a 1% sodium tetra borate solution. Slides were placed on a hotplate and a drop of the stain solution added to the specimen for 30 seconds. The stain was rinsed off in tap water for a further 30 seconds.

4',6-Diamidino-2-phenylindole (DAPI)

Slides were passed through xylene 2×7 minutes then through a series of graded alcohols for rehydration:
- 100% 5 minutes;
- 70% 5 minutes;
- 50% 5 minutes;
- Distilled water for 5 minutes.

The slides were gently blotted dry of excess water before adding 50 µl of a 1:300 DAPI solution to the slides for 5 minutes at room temperature. The slides were subsequently rinsed in PBS/Tween for 3×5 minutes. The slides were mounted with a drop of Fluoromount and cover slipped.

Specimen Processing for Electron Microscopy

Both laminated and delaminated cholecyst and small intestine samples were prepared for electron microscopy. Fixation was via a 3% Glutaraldehyde Fixative for at 48 hours. Samples were prepared for both scanning and transmission electron microscopy.

Scanning Electron Microscopy

Samples were removed from fixative and subjected to dehydration by immersion in graded alcohols, as given by the following dehydration procedure:
- PBS 5 minutes;
- 10% ethanol 5 minutes;
- 25% ethanol 5 minutes;
- 50% ethanol 5 minutes;
- 70% ethanol 5 minutes;
- 90% ethanol 5 minutes;
- 100% ethanol 5 minutes;
- 100% acetone 5 minutes.

Samples were placed in a desiccator overnight to allow complete dehydration. Following dehydration samples were mounted on studs via carbon adhesive plaques and gold coated in an Emitech K-550X Sputter Coater for 2 minutes.

Transmission Electron Microscopy

Samples were removed from fixative and cut into 2 mm×2 mm pieces before being rinsed in PBS 3×5 minutes. Samples were then immersed in a 1% osmium tetroxide ($OSO_4$) PBS solution for 2 hours. Samples were subsequently dehydrated in graded alcohols:
- 50% ethanol 10 minutes;
- 70% ethanol 10 minutes;
- 90% ethanol 10 minutes;
- 100% ethanol 10 minutes.

Samples were place in place in 10 ml glass vials to which was added propylene oxide ($C_3H_6O$) for 20 minutes, this was removed and then a 50:50 mixture of propylene oxide and embedding resin was added. Sample remained in this solution for 8 hours on a Luckham Multimix Major roller.

Resin for embedding was TAAB Spurr, which was prepared immediately before use according to supplied instruction. Samples were placed in this resin for 24 hours in 10 ml glass vials on the roller. Samples were then placed in TAAB C094 embedding capsules and incubated for 48 hours at 60° C. Blocks were then trimmed and cut on a Reichert—Jung Ultracut microtome.

Specimen Staining for Scanning Electron Microscopy

Sections for toluidine blue staining were cut to 1 µm in thickness, these sections were used as scout sections for the identification of a suitable area to procure sections for transmission electron microscopy. Sections were placed on Agar 200 copper grids and stained with heavy metals for viewing.

Grids were placed in a rubber slide holder and immersed in 0.5% uranyl acetate ($UO_2(CH_3COO)_2 2H_2O$), $(CH_3COO)_2 \cdot 2H_2O$) for 40 minutes. Following immersion in uranyl acetate the grids were rinsed in ultrapure $H_2O$ then placed in a 50% methanol solution for 1 minute followed by a further rinse in ultrapure $H_2O$. Grids were then immersed Reynolds in lead citrate solution for 5 minutes. The grids were placed still in their rubber holder, within a petri dish containing NaOH pellets to remove carbon dioxide. The grids were finally immersed in ultrapure $H_2O$ for 1 minute.

Viewing Apparatus

| | |
|---|---|
| (A) Light Microscopy | Olympus BX51 fluorescent microscope. |
| (B) Scanning Electron Microscopy | Hitachi S-4700 scanning electron microscope. |
| (C) Transmission Electron Microscopy | Hitachi H-7600 transmission electron microscope |

Cell Numbers

Cell numbers present in tissue were investigated using image analysis software. Digital images obtained from paraffin embedded sections were accordingly stained and analysed. Areas of 0.1 mm$^2$ were identified and cells within counted. Area grids overlapped into that of the previous area. 10 counts were taken per slide section. Eighteen individual slides were analysed, nine being sections cut from the isolated small intestine submucosa and nine from the isolated cholecyst extra cellular matrix.

Cross Linking mTGase (Activa® WM, Ajinomoto Co. Inc.), which had been purified by cation-exchange chromatography can be used at various concentrations for cross-linking the isolated tissue. The specific activity of mTGase was determined to be 27000 nmol putrescine incorporated/mg/hour. The mTGase was supplied in 20 mg (dry weight) samples, which were subsequently dissolved in 20 ml of deionised $H_2O$ and stored at $-20°$ C. Various concentrations of mTGase (0.01-0.03%) can be used cross-link tissue at $45°$ C. The tissue is then cooled to room temperature ($22°$ C.).

In Vitro Studies

Two independent studies were carried out in order to appraise the behaviour of 3T3 fibroblasts when in contact with mTGase, with emphasis on its capacity to support cell adhesion and cell growth. Firstly, to facilitate the investigation of any adverse effect on cell viability and cell proliferation in the presence of mTGase, 3T3 fibroblasts were cultured in 6-well tissue culture plates containing 3ml of Dulbecco's Modified Eagle Medium (DMEM) supplemented with 10% fetal bovine serum (FBS) and 1% penicillin/streptomycin (Pen/Strep), in addition to 0.05%, 0.005% and 0.0005% mTGase (Control wells were comprised of medium and cells only). Cells were seeded at a density of $1\times10^5$ cells/well and cultures were maintained at $37°$ C. in a 5% $CO_2$ humidified incubator for up to 72 hours. Experiments utilised triplicate samples per concentration variant, and cell viability and cell proliferation were examined using trypan blue staining and AlamarBlue™ assays, respectively, after 24 and 72 hours incubation.

A second study was carried out in order to evaluate the cytocompatibility of 4% w/v gelatin gels cross-linked with 0.01-0.03% mTGase, after 24, 48 and 72 hours incubation. Tissue culture grade polystyrene was used as a control substrate. Thin gels (cross-linked and untreated) were cast in 6-well tissue culture plates under sterile conditions. All sterile equipment, including magnetic stirrers and containers were utilized and production was carried out in laminar flow cabinets. Both the protein and the enzyme were passed through sterile filters to ensure sterility. The gels were stabilised at room temperature for 5 hours followed by rinsing with 1% Pen/Strep solution and Hank's Balanced Salt Solution (HBSS, Sigma Chemicals). 3T3 fibroblasts were seeded on each substrate at a cell density of $1\times10^5$ cells/well and grown in DMEM medium supplemented with 10% FBS and 1% Pen/Strep. Three samples were employed with each concentration variant, and cell viability and cell proliferation were examined using trypan blue exclusion methods and AlamarBlue™ assays, respectively, after 24, 48 and 72 hours incubation at $37°$ C. in a 5% $CO_2$ humidified incubator.

In further embodiments of the invention, such as those exemplified in FIGS. 24-28, CEM was isolated from the cholecysts of 12-18 month old market weight pigs within 2 hours of animal slaughter. The CEM isolation technique involved draining the bile from the cholecyst, removing the fundus and neck regions and cutting the remaining cylindrical piece of tissue to create a rectangular section of cholecyst. The mucosal layer was removed in long wiping motions with a blunt edge, the tissue was turned over and the serosal side was pealed off with a forceps, leaving the extra cellular matrixl layer. Isolated CEM was rinsed in phosphate buffered solution (PBS) (Sigma-Aldrich, Dublin, Ireland. All reagents were purchases from Sigma-Aldrich Ireland, unless otherwise stated). Orientation of the excised tissue was recorded during the isolation procedure and isolated samples of CEM were cut into asymmetrical sections, which facilitated later identification of the mucosal and serosal sides of the material and the orientation of each sample.

CEM topography

CEM from five cholecysts was fixed in 2% glutaraldehyde/PBS for 24 hours at room temperature and pressure. Two samples, measuring approximately 10 mm*10 mm, were isolated from the central region of each cholecyst and prepared for SEM analysis through dehydration in graded alcohols (30%-100%) followed by two 15 minute exchanges in absolute alcohol and chemical drying in hexamethyldisilazane (HMDS). One serosal-side-up and one mucosal-side-up sample from each organ was mounted on carbon stubs and a 4 nm thick coating of gold was applied with the ion beam sputter coater (Emitech K550, Emitech Ltd., Kent, England).

The low voltage, high resolution SEM (s-4700 Hitachi Scientific Instruments, Berkshire England) was used to capture photomicrographs of both the mucosal and serosal sides at 15 kV and at magnifications ranging from 1,000× to 15,000×. Three stereo pairs captured from random locations on each side of each sample at 15,000× and at angles of $0°$ and $5°$ were used to create virtual three dimensional images of the surface topography. Elevation height, a three-dimensional feature, was quantified by viewing the stereo pairs under a stereoscope and using the formula:

$$Z = \frac{P}{2\mathrm{Sin}(\alpha/2)} \quad \text{Equation 1}$$

Where Z is feature height, a is half of the angle of the stereo pair and P is the parallax, the latter of which was measured with a stereo viewer. One of the images from each pair was then used to measure pore and fiber diameters on the surface with image analysis software (Image Pro®, Media Cybernetics, Berkshire, England). Due to the non-uniform non-circular shape of pores on the material surface pore diameter measurements were taken at the widest part of the pore and always in the vertical direction. In all cases 10 features were measured per photomicrograph or stereo pair and the location of particular features measured were chosen by superimposing a numbered grid on the photomicrograph and using statistical tables of random numbers to select locations from which to take measurements.

CEM Collagen Fiber Orientation

Asymmetrical samples of CEM (n=5), fixed similarly to those for SEM analysis, were viewed under circularly polarised light with the Metripol Birefringence Imaging Module® (Oxford Cryosystems Ltd., Oxford, England), which was attached to a light microscope (Prior). The polarisation module, consisting of a series of specialised filters, an analyser and a rotating polariser, was used to produce a ray of polarised light which split into two mutually perpendicular vibrating rays as it passed through the birefringent CEM specimen. Retardance of one ray relative to that of the other was then measured by the microscope. For each area of CEM examined 50 views were captured by a CCD camera at $3.6°$ intervals and merged to create a composite image of the area; this process was facilitated by the rotating polariser. Composite images captured by the microscope consisted of three images: an orientation image depicting collagen orientation, a birefringence image, demonstrating levels of birefringence of the area under investigation and an intensity image representing light intensity. Data in these images was stored as pixels whereby, pixel colours corresponded to a given legend and represented collagen fiber angle for the particular pixel.

To calculate the preferred collagen fiber orientation the number of pixels of a particular colour in the orientation images was quantified using image analysis software (Image Pro®) and the percentage area of the sample under the microscope with fibers oriented at a particular angle was calculated. All samples were examined at 40× and 100×, but for image analysis and statistical analysis purposes five composite images of each sample were captured at random locations at 100× and the orientation images were analysed. In all cases filter 5 which operates at a wavelength of 600 nm was used to polarise the light and all images were taken on the slow axis of the indicatrix. Heart valves, whose collagen fiber orientation has previously been characterised, were used as a control (18).

CEM Biaxial Tests

Equi-biaxial mechanical tests were preformed on sections of CEM to identify the stiffness of the material along the axes parallel and perpendicular to the preferred collagen fiber orientation, as elucidated by polarised light microscopy. A biaxial fixture was designed in conjunction with Zwick GmbH & Co. KG (Ulm, Germany) and consisted of 4 100N load cells, attached to a clamping mechanism via poly-par-aphenylene terephthalamide (Kevlar®, DuPont Engineering Fibers, Geneva, Switzerland) pulley cables. The clamping mechanism was a combination of four fishing hooks on each side of the sample, connected by Kevlar® and attached to the pulley cables via a small stainless steel tab. All samples tested were clamped prior to loading onto the biaxial fixture in an effort to reduce mounting strains. The biaxial fixture was attached to the Z5000 Zwick Universal testing machine (Zwick GmbH & Co. KG). Samples of isolated CEM (n=8), approximately 2 cm*2 cm, were biaxially loaded parallel to and perpendicular to the directions of preferred collagen fiber orientation. A preload of 0.01N was applied to all load cells prior to commencing each test and all samples were fully loaded and unloaded twice to precondition. CEM samples were loaded three times at a strain rate of 1.27 mm/min to 1.2N. All tests were carried out in the water bath at 37° C. CEM thickness was 0.35 mm.

Results

The results have been divided into sections, gross morphology, light microscopy, electron microscopy, cell numbers, in vitro studies. The gross morphology section addresses the gross structural characteristics of the cholecyst and small intestine submucosa following delamination and comparisons between these two scaffolds are made. The section on light microscopy deals with these two materials on a microscopic level, while the electron microscopy section investigates the ultrastructural properties of these tissues.

Gross Morphology

Tissue measurements

Measurements were obtained using an AP-6500 Micrometer screw gauge. Relative thickness of the tissues was obtained before and after delamination of the extra cellular matrix. Delaminated tissue represents the extra cellular matrix of that tissue. Measurements were obtained from tissue obtained from 9 separate animals prefixation. The unprocessed cholecyst only measured an average of 0.4 mm, in contrast to the far thicker unprocessed small intestine, which measured an average of 4.9 mm. However the isolated cholecyst extra cellular matrix (0.126 mm) transpired to be thicker than that of the isolated small intestine submucosa (0.0718 mm). The small intestine isolated submucosa also exhibited a relatively large standard deviation in comparison with the isolated cholecyst extracellular matrix Images were acquired of cholecyst and small intestine tissue before and after delamination, allowing for the comparison of gross characteristics of the tissues.

Figure 7:
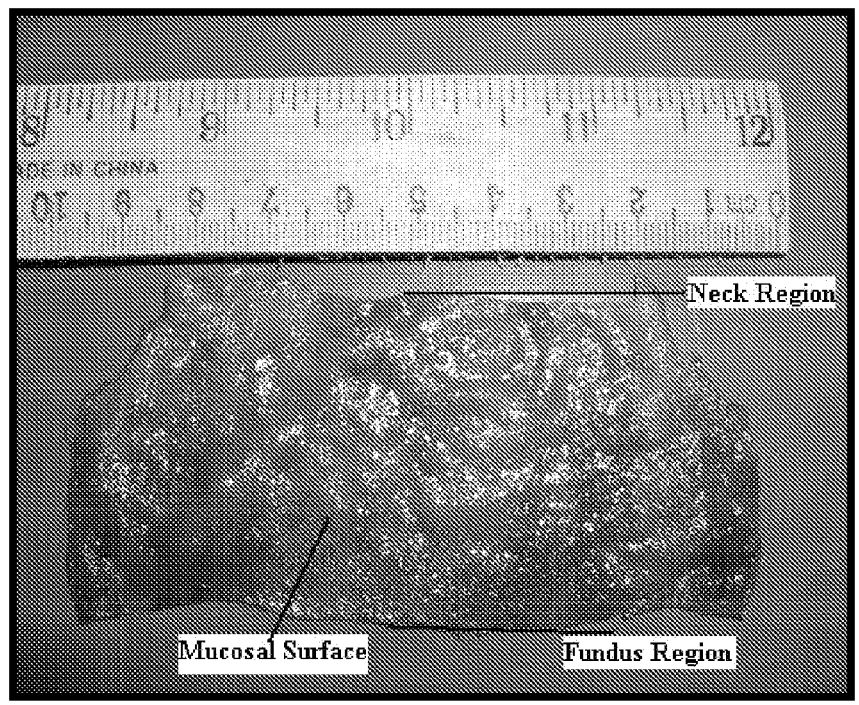
FIG. 7: The laminated cholecyst.

The cholecyst was seen to be a relatively thin-walled organ that was easily transformed into a flattened sheet by removal of the fundus and neck region and a single longitudinal incision (see FIG. 7). The mucosa was seen to be a smooth undulating surface that was covered by a thin film of mucus and bile, which was removed along with its underlying lamina propria and poart of the muscularis layer, during the peeling process. The tissue remained highly flaccid and malleable even following extended fixation. Remainder of the muscularis layer was carefully removed to expose the mucosal side surface of the cholecyst extracellular matrix. The resulting sheets were approximately 10 cm in length and 5 cm in width.

The underlying serosal side layers were removed with a pair of round tipped forceps. This mesothelial layer and the adipose tissue layers were removed as a single entity, resulting in the intact extracellular matrix of the cholecyst wall.

Figure 8:
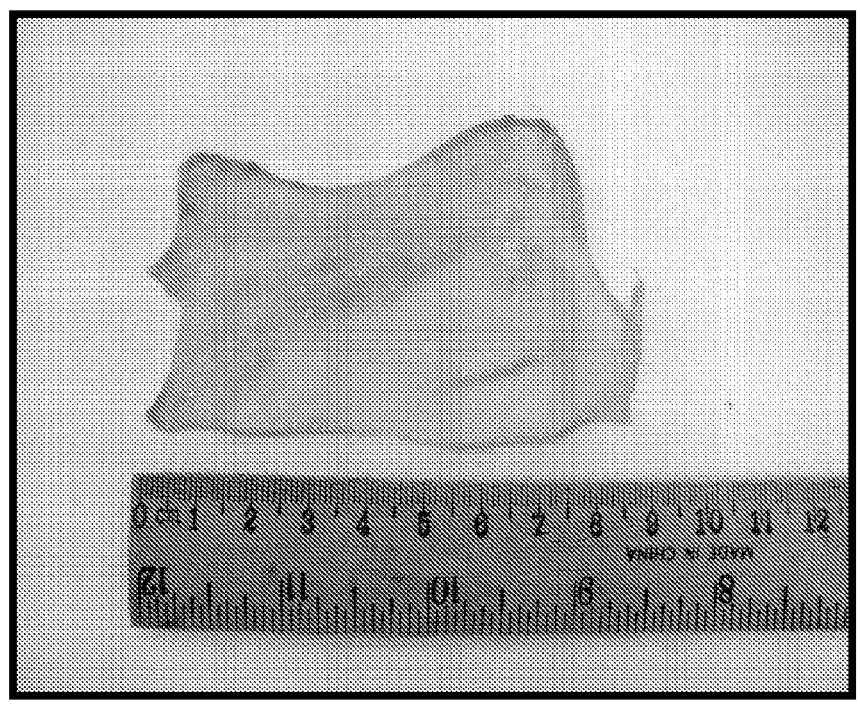
FIG. 8: Isolated cholecyst extracellular matrix.

The isolated cholecyst extracellular matrix appeared as a semitransparent membrane without any remarkable surface features (see FIG. 8). It was of uniform thickness throughout its entirety and had a glistening moist appearance.

Figure 9:
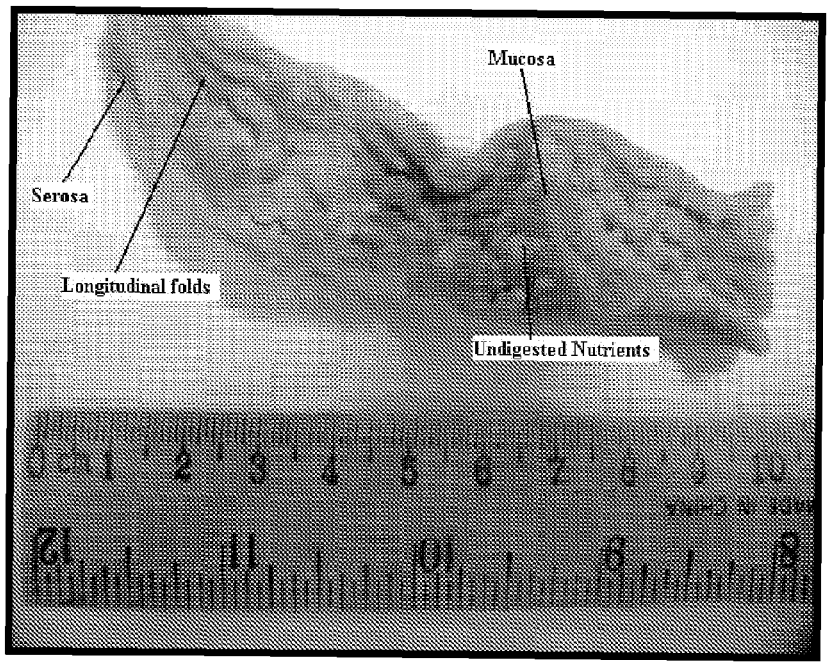
FIG. 9: Segment of the laminated jejunum.

The jejunum segments were tough and relatively thick walled segments of tissue (see FIG. 9). The lumen was all but obliterated by the extensive mucosa, which was thrown into numerous longitudinal ridges similar in appearance to the rugae of the stomach, no plicae circulares were observed. This mucosa was relatively difficult to remove, requiring greater force and diligence to remove than that of the cholecyst. The mucosa was clearly visible while being removed, forming a clumped mass of cellular material once removed. Undigested debris also was visible within the jejunum lumen. The intestinal tissue was stiff and tended to return to the in vivo conformation spontaneously, i.e. a tubular structure.

Figure 10:
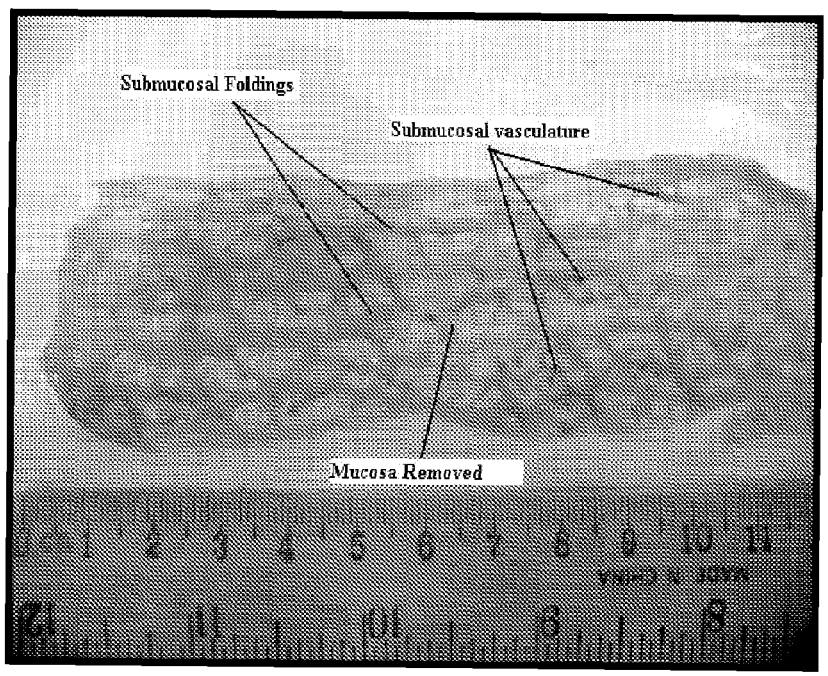
FIG. 10: Isolated small intestine extracellular matrix.

The isolated small intestine submucosa was shown to consist of a non-uniform, almost transparent film of tissue (see FIG. 10). The numerous ridges of the mucosa were still apparent at the level of the extra cellular matrix, forming local, interconnecting ridge-like thickenings along the mucosal side of the extra cellular matrix only. This extra cellular matrix scaffold also demonstrated extensive vascular tissue throughout its length, which was readily visible to the naked eye.

A direct comparison between cholecyst extra cellular matrix and small intestine submucosa (FIG. 6-10) shows the discrepancies in surface morphology and allows the visualisation of the relative thickness between the two tissues and the amount of vascular tissue present.

Light Microscopy

Light microscopy revealed the microstructure of the small intestine and cholecyst tissue before and after the delaminating process. Cells and cell nuclei are easily discernable from the surrounding connective tissue. Epithelial cells are also evident in the micrographs, identifiable as definitive epithelia at the extremities of the tissue mucosa. Haematoxylin and eosin (H&E) revealed the general structure of all sections, haematoxylin staining acidic structures i.e. DNA of the nucleus a blue-purple colour and eosin staining the basic cytoplasmic structures a light pink colour. Van Gieson's stain (G) resulted in the identification of connective tissue, staining collagen a deep red colour. Nuclei are also stained blue in these images while cytoplasm and erythrocytes are stained a pale yellow colour. Toluidine blue (T) resulted in the monochromatic staining of sections in various shades of blue, the nuclei being stained the most intensely, and the connective tissue a lighter shade of blue. Scale bars were used to confirm image measurements.

Figure 11:
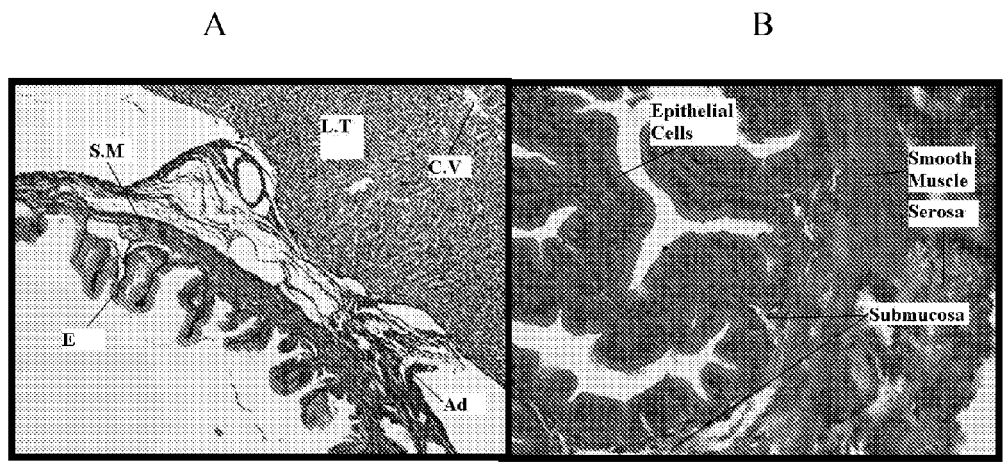
FIG. 11: Histology of cholecyst wall attached to liver (A) VG X 100, small intestine wall (B) VG X 400.

FIG. 11A demonstrates the microstructure of the laminated cholecyst attached to the liver. The mucosal surface is clearly evident as a continuous epithelium of yellow stained cells, E while the underlying lamina propria, L.P., and its underlying muscularis appears deep red in colour, cholecyst extracellular matxix, ECM lies in between the muscularis and the adeventetia in the region attached to the liver, L.T., here the serosal layer is replaced by a thick connective tissue called adventitia, Ad. A central venule in liver tissue is also seen, C.V. FIG. 11B, presents the typical microstructure of small intestinal wall with mucosal epithelial cells, lamina propria, submucosa, thick muscle and serosal layer.

Figure 12:
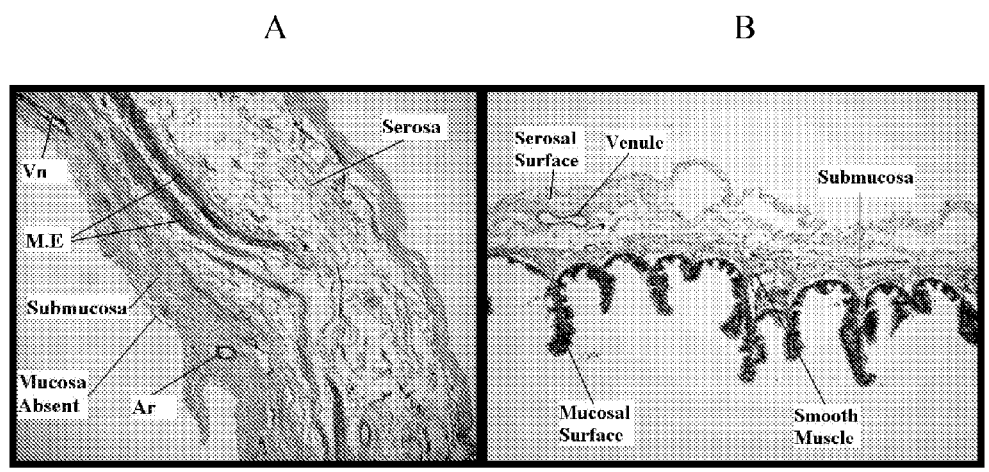
FIG. 12: Histology of cholecyst wall H&E X100 (A), H&E X40

The different layers in the part of cholecyst wall that is not attached to the liver, can be clearly seen in the histology FIG. 12A &B. The cholecyst wall is lined on its luminal surface with a simple columnar epithelium. The mucosa rests on a basement membrane, which is continuous with the lamina propria. Lamina propria is rich in fenestrated capillaries and small venules. External to the lamina propria is a thin muscularis layer with numerous smooth muscle bundles interlaced with collagenous fibres running in longitudinal and circumferential directions of the cholecyst wall. Muscularis layer is followed by a relatively acellular ECM made of loosely braided collagen bundles. In the portion of cholecyst, which is in direct contact with the liver, this fibrous ECM connects to the liver. Elsewhere, this layer is covered by a relatively thick adipose tissue innervated with large blood and lymphatic vessels. This tissue is also reported to have autonomic nerves that innervate the muscular layer (ref). The adipose tissue is covered by serosa, which is made of thin layers of loose connective tissue and peritoneal mesothelium. The submucosa is lacking and its muscularis layer, unlike that of intestine, is not made of purely muscular tissue. Instead, it is made of varying amounts of muscle tissue arranged loosely intertwined with collagenous fibres. In other words, a separate muscularis externa is not evident.

Figure 13:
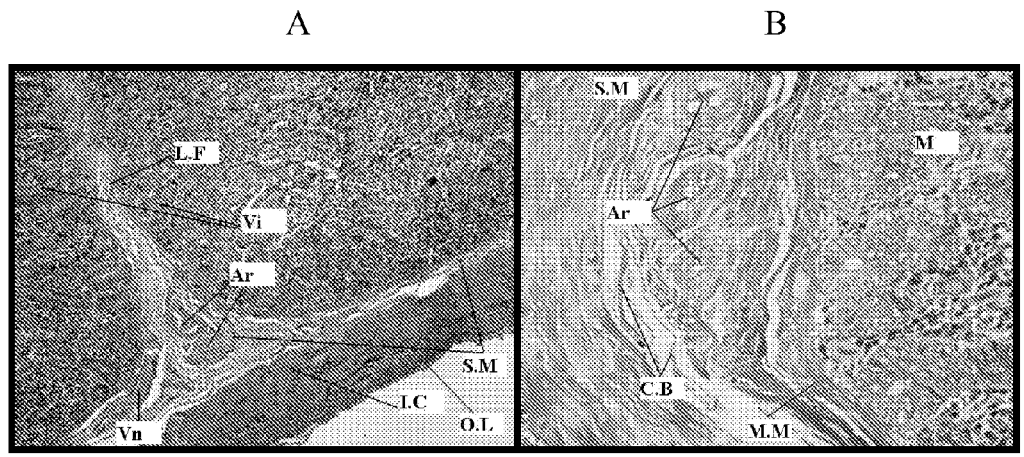
FIG. 13: Histology of small intestine wall H&E X100 (A), VG X400 (B)
Figure 14:
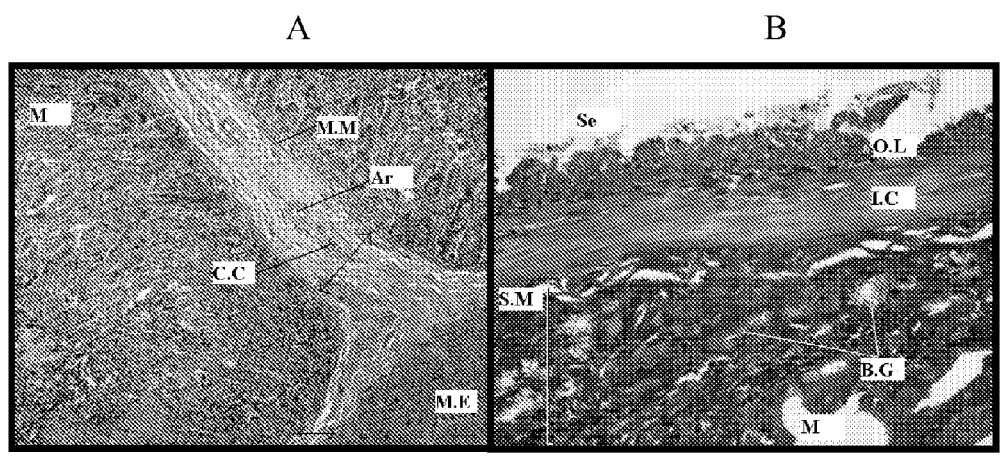
FIG. 14: Histology of Mucosal fold of small intestine H&E X 100 (A), Duodenum VG X400 (B).

As shown in FIG. 13(A) the extensive mucosa of the jejunum and the arrangement of the intestinal villi, Vi. A large longitudinal fold, L.F., is also strikingly evident in the centre of the image. Also is seen is the large discrepancy in the submucosal thickness throughout the tissue. The vascular nature of the submucosa, S.M., is indicated by the presence of numerous arterioles, Ar, and a large venule, Vn. This micrograph also demonstrates the organisation of the external muscle layers, the inner circular, I.C., and outer longitudinal, O.L., clearly visible. (B) The connective tissue of an expanded region of the jejunum submucosa, S.M. Large bundles of red stained collagen, C.B., are visible within this layer, as are numerous vessels of the portal system, Ar The muscularis mucosae, M.M., is seen in the right of the micrograph, separating the mucosa, M, from the underlying submucosa FIG. 14 shows (A) the jejunum submucosa can be seen to extend up into a prominent fold, into the mucosa, M, the submucosa being thicker here than the submucosa not associated with the fold. The cellularity of the small intestinal submucosa is demonstrated by the presence of numerous arterioles, Ar, and cell clusters, C.C., probably fibroblasts. The two muscular layers, the muscularis mucosae, M.M., and the muscularis externa, M.E., are also visible. (B) demonstrates the presence of glands of Brunner, B.G., within the submucosa of the duodenum. Here the connective tissue content of the submucosa is reduced and the cellular content markedly increased, the ECM only present in scant bundles and a thin layer adjacent to the inner circular smooth muscle, I.C., The outer longitudinal muscle, O.L., and serosa, Se, is also evident.

Figure 15:
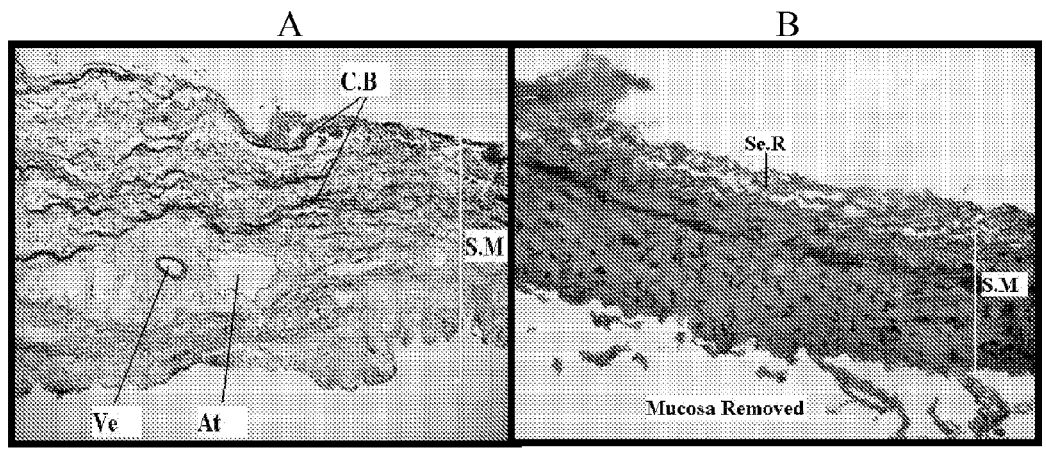
FIG. 15: Isolated cholecyst extracellular matrix scaffold (A) VG X 400, (B) H&E X 400.

As shown in FIG. 15 the porcine submucosa, S.M., was abundant in collagenous connective tissue, C.B., and remarkably less cellular than other layers, the tissue contained relatively few arterioles and venules, Ve, yet scattered cells are observable within the connective tissue matrix of the submucosa (B), though other areas contained very few cells (A). Occasionally delamination produced imperfection, such as the submucosal damage, Se.R, evident in micrograph (B) and the artefacts, At, observable in micrograph (B).

Figure 16:
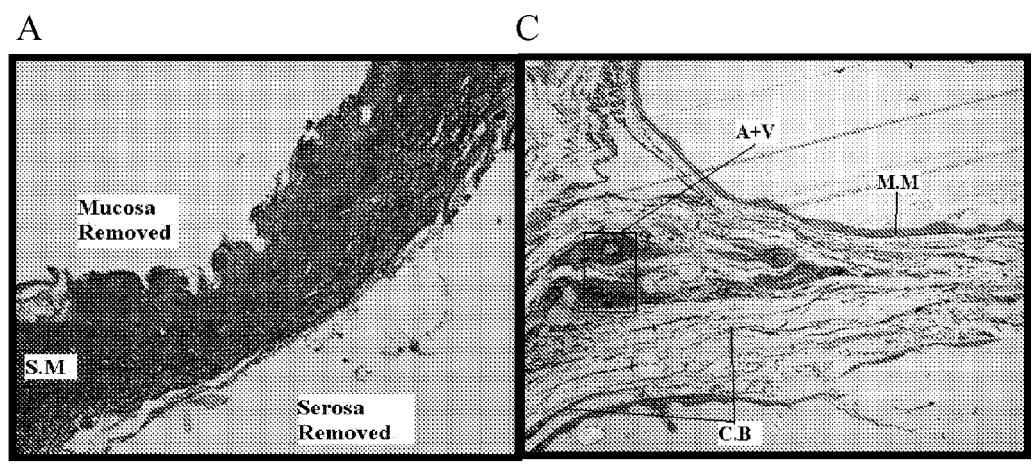
FIG. 16: Histology of Isolated cholecyst extracellular matrix H&E X400 (A), isolated small intestine submucosa TB X400 (B).

The collegenous nature of the porcine cholecyst extracellular matrix is evident in FIG. 16(A) from the pink staining of the extra cellular matrix connective tissue. Very few cell nuclei are observable. (B) The muscularis mucosae, M.M., has been preserved on the delaminated small intestine submucosa. Large bundles of collagen, C.B., are evident, as is a paired arteriole and venule, A+V.

Electron Microscopy

Electron microscopy revealed the fine ultrastructure of the extra cellular matrix scaffolds, fiber orientation, and density and cellularisation were observed via scanning electron microscopy (SEM) and transmission electron microscopy (TEM). Scale bars and magnification factors are included in the ultramicrographs.

Figure 17:
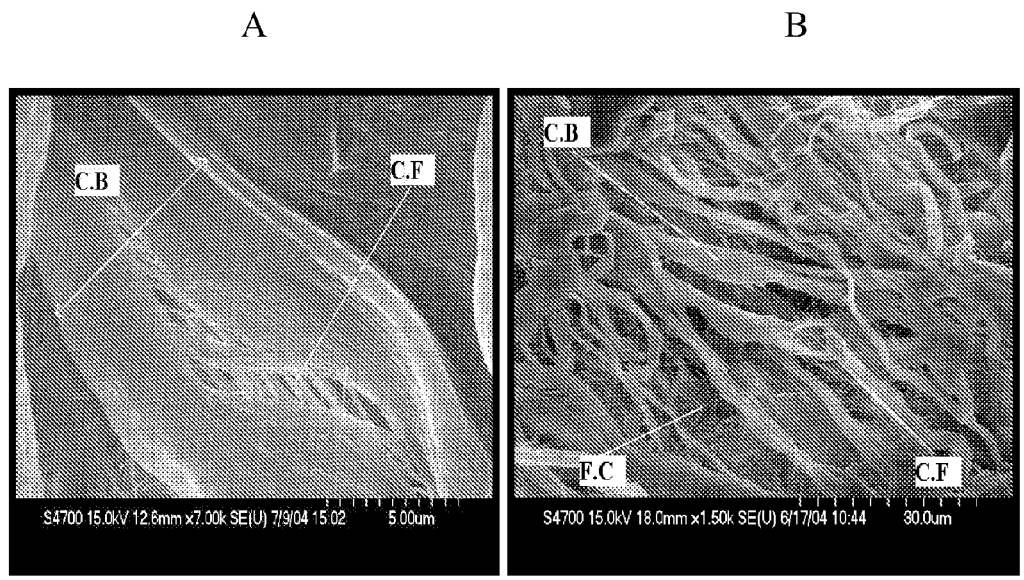
FIG. 17: Scanning electron micrographs of cholecyst extracellular matrix x7000 (A) and x1500 (B).

The fine ultrastructure of the extra cellular matrix can be seen in FIG. 17(A) Collagen bundles, C.B., are seen to be formed of many fine threadlike collage fibrils C.F., (B) A meshwork of collagen bundles forms the bulk of the tissue, yet smaller fibers not associated with larger collagen bundles form a fine mesh-like fibrous component, F.C., of the tissue.

Figure 18:
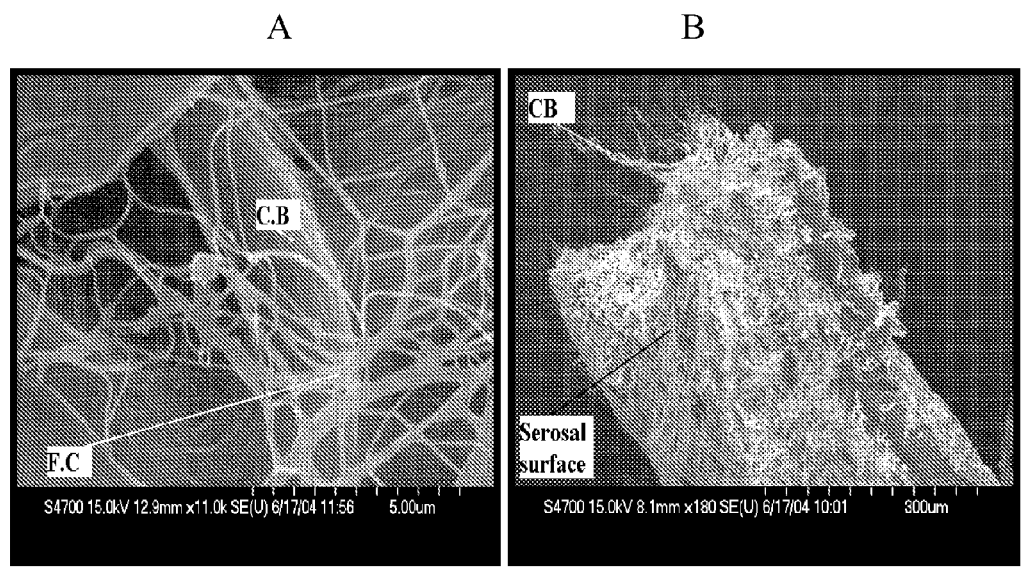
FIG. 18: Scanning electron micrographs of cholecyst extracellular matrix x11000 (A) and x180 (B).

The fibrous nature of the matrix with interwoven bundles of collagen (C.B.) (FIG. 18). The fine filamentous non-collagenous content of the CEM is also clear (F.C.), forming a fine weave between the collagen bundles, C.B.

Figure 19:
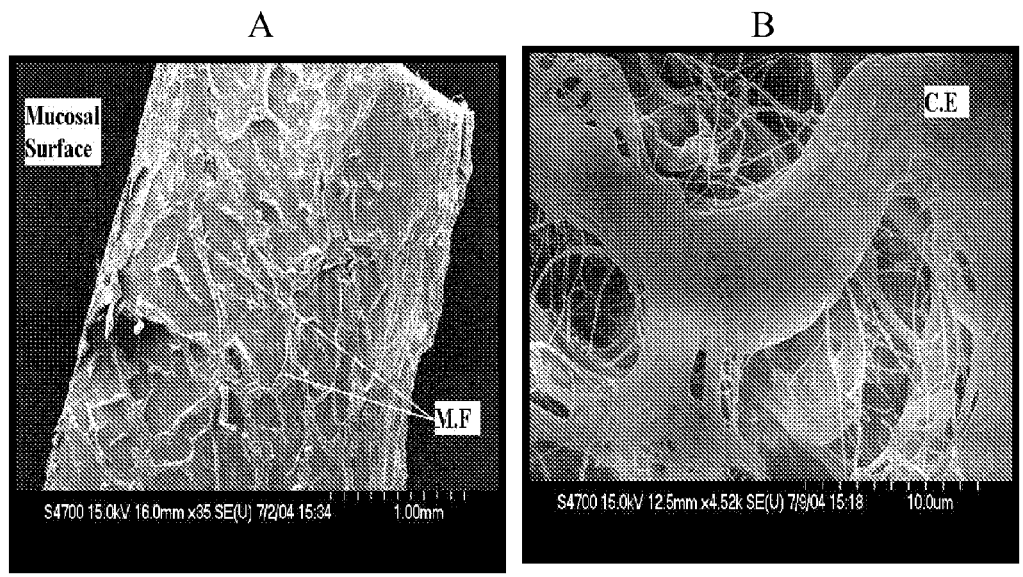
FIG. 19: High mag. (A) and low mag. (B) cholecyst extracellular matrix. SEM.

Surface mucosal foldings, M.F., are evident in FIG. 19(A), on this low magnification image raising the mucosal into numerous ridges. (B) A large mass in the centre of this image, possibly a cellular extension, C.E., is seen in association with many fine fibers, passing over and around the extension.

Figure 20:
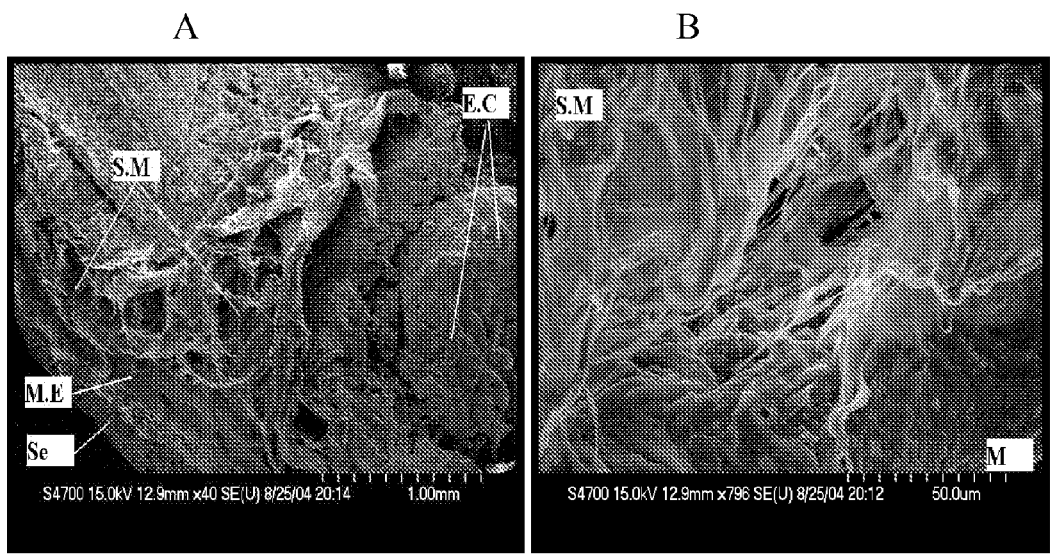
FIG. 20: Scanning electron micrographs of small intestine submucosa, x40 (A) and x796 (B).

The laminated structure of the small intestine is evident in FIG. 20(A) as well as the course fibrous nature of the submucosa S.M., The external muscle layers, M.E., serosa, Se, and epithelium of the mucosa, E.C., are all evident. A large longitudinal fold occupies the centre of this image. (B) The submucosal-mucosal border is evident, the submucosa recognisable by its highly fibrous nature, while the mucosa appears as a tightly packed dense array of cells.

Figure 21:
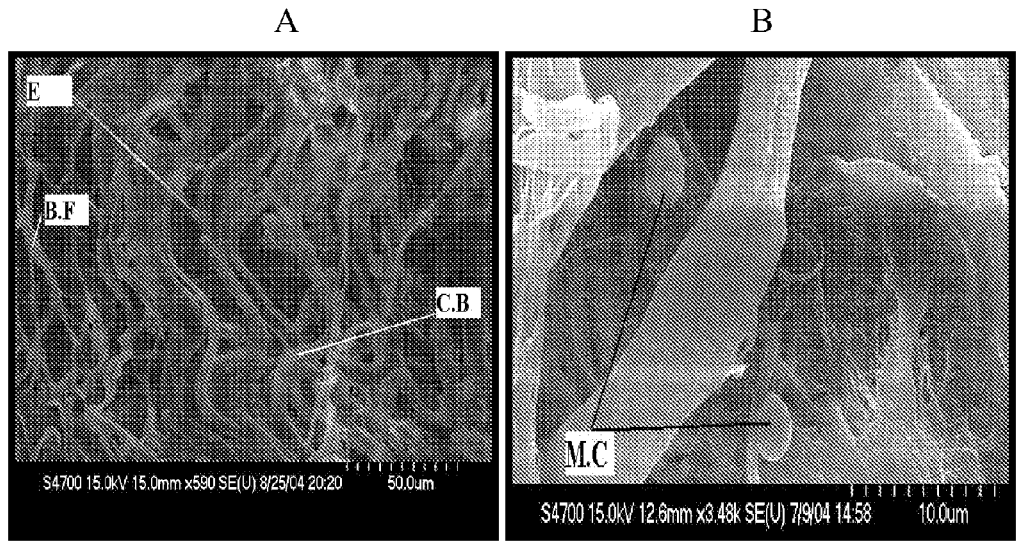
FIG. 21: Scanning electron micrographs of small intestine submucosa, x590 (A) and x3480 (B).

FIG. 21(A) is a low powered micrograph of collagen orientation within the small intestine submucosa. The collagen bundles, C.B., are orientated in parallel arrays and have adopted a corrugated conformation. These bundles are seen to form branching networks of fibers, B.F., within this connective tissue. Several erythrocytes can be seen adhering to these fibers, E. (B).

Figure 22:
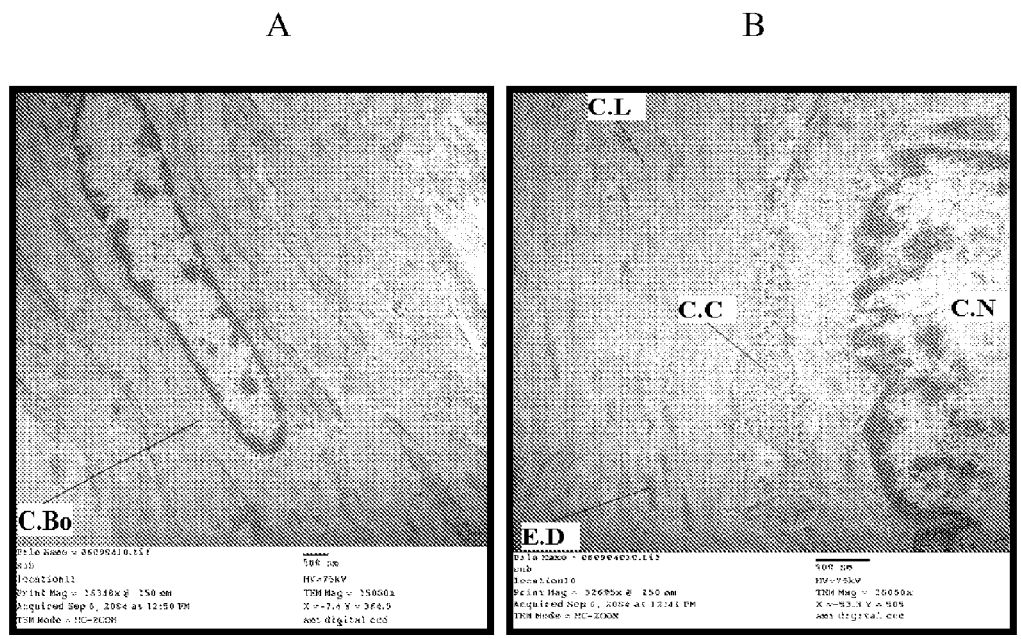
FIG. 22: Transmission electron micrographs of cholecyst extracellular matrix x15000 (A) and x30000 (B).

As can be seen in FIG. 22(A) a fibroblast is present in the centre of the image. The cell has an elongated appearance, yet cellular extensions are not visible. Large amounts of nuclear euchromatin indicate cells to be active, however the machinery of synthesis such as Golgi apparatus and rough endoplasmic reticulum are not evident. Surrounding the cell large amounts of collagen are evident in longitudinal, transverse and oblique orientation. (B) A collagen bundle in cross section, C.C., reveals the individual collagen fibrils. Collagen can also been seen in longitudinal section, C.L., Dark areas of elastin deposits are also present, E.D.

Figure 23:
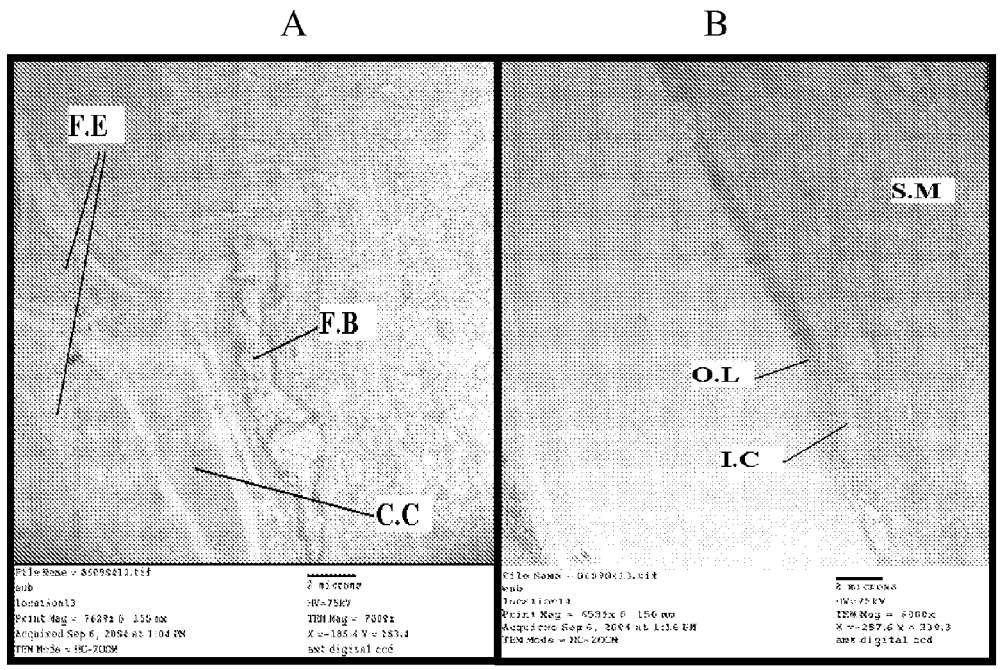
FIG. 23: Transmission electron micrographs of small intestine submucosa x7000 (A) and x4300 (B).

In FIG. 23(A) extension from an active fibroblast, F.E., are prominent on the left side of this image, being easily recognisable by their high content of rough endoplasmic reticulum and Golgi apparatus. The cell nucleus is barely visible at the extreme left of the image. The extensions pass around a large bundle of collagen in cross section, C.C., and seem to abut on a nearby cell probably another fibroblast, F.B., (B) A section of the muscularis mucosae is seen to remain following delamination of the cholecyst. The outer longitudinal, O.L., and inner circular, I.C., muscle are indicated. The nuclei of a extra cellular matrix, S.M., fibroblast is also evident at the extreme top right of the image.

Cell Numbers

Cell numbers were larger almost by a factor of two in the isolated small intestine submucosa. Here cell numbers averaged 44.2 per $cm^2$ Cell numbers in the cholecyst extracellular matrix averaged at 22.35 cells per $cm^2$ Large discrepancies in cell numbers were observed between different regions of a sample, as well as between different sections. Both tissues exhibited a relatively large standard deviation in mean cell numbers.

In Vitro Studies

In vitro studies of mTGase monitored the activity of 3T3 fibroblasts cultured in various concentrations of mTGase after periods ranging between 24 and 72 hours.

TABLE 1

Cell Viability After 24 and 48 h (Trypan Blue Exclusion)

| Gel Type | No. of Cells (SEM) | |
|---|---|---|
| | 24 h | 48 h |
| Control | 311333 (6110.1) | 1016000 (52000) |
| 0.05% mTG | 189667 (7767.5)[a] | 74667 (9451.6)[a] |
| 0.005% mTG | 255222 (5131.6)[a] | 1004667 (46231.3)[a] |
| 0.0005% mTG | 276667 (18147.5)[a] | 1042000 (58206.5) |

[a]Indicates significant difference from control (untreated media) ($p < 0.05$) (n = 3)

Table 1 summarises the effect of mTGase on the number of viable cells at 24 and 72 hours using the trypan blue exclusion method. After 24 hours, there was a significant decrease ($p < 0.05$) in the number of viable cells in all concentrations of mTGase when compared to the control (medium and cells). At 72 hours, there was a significant decrease in viable cell number ($p < 0.05$) observed between the highest concentration (0.05%) of mTGase and the control, indicating cytotoxicity.

TABLE 2

Cell Proliferation After 24 and 48 h (AlamarBlue ™ Assay)

| Gel Type | Fluorescence (SEM) | |
|---|---|---|
| | 24 h | 48 h |
| Control | 27966.89 (503.5) | 52113.4 (1810.2) |
| 0.05% mTG | 16762.89 (817.1)[a] | 5573.6 (1290.5)[a] |
| 0.005% mTG | 23869.22 (348.9)[a] | 51253.4 (2131.3) |
| 0.0005% mTG | 25963.55 (1084.8) | 52949.07 (1934.7) |

[a]Indicates significant difference from control (untreated media) ($p < 0.05$) (n = 3)

Table 2 demonstrates the effect of exposure to similar concentrations of mTGase on the cell proliferation after 24 and 72 hours. Results after 24 hours showed a significant decrease ($p < 0.05$) in the activity of cells in the presence of 0.05% and 0.005% mTGase, with 0.05% mTGase showing the lowest level of cell proliferation. After 72 hours, a significant decrease ($p < 0.05$) was noted in cell proliferation levels, where exposed to 0.05% mTGase. No significant difference ($p < 0.05$) was detected between low levels of mTGase (0.005% and 0.0005%) and the control.

Tables 3 and 4 quantify the results obtained from the trypan blue exclusion and the AlamarBlue™ assays, respectively, where cells were seeded on gelatin film substrates cross-linked with various concentrations of mTGase.

TABLE 3

Cell Viability After 24, 48 and 72 h (Trypan Blue Exclusion)

| Gel Type | No. of Cells (SEM) | | |
|---|---|---|---|
| | 24 h | 48 h | 72 h |
| Control | 181333 (4163.3) | 370000 (8888.2) | 772667 (25716.4) |
| Gelatin | 181333 (7234.2) | 389000 (9643.7) | 773333 (25006.7) |
| 0.01% mTG | 140000 (6557.4)[a] | 298667 (12342.3)[a] | 711333 (24684.7) |
| 0.02% mTG | 140000 (2645.8)[a] | 304333 (9504)[a] | 706333 (17039.2) |
| 0.03% mTG | 132667 (4725.8)[a] | 287667 (4041.5)[a] | 672667 (49003.4)[a] |

[a]Indicates significant difference from control (untreated media) ($p < 0.05$) (n = 3)

Table 3 shows the number of viable cells on each substrate after 24, 48 and 72 hours. There was a significant decrease $p < 0.05$) in cell viability on mTGase cross-linked gelatin films after 24 hours compared to the control. A similar trend was seen after 48 hours cultivation, but at 72 hours, only cell growth on 0.03% mTGase-cross-linked gelatin was significantly different ($p < 0.05$) from the control.

TABLE 4

Cell Proliferation After 24, 48 and 72 h (AlamarBlue ™ Assay)

| Gel Type | Fluorescence (SEM) | | |
|---|---|---|---|
| | 24 h | 48 h | 72 h |
| Control | 26955.10 (1299.1) | 36813.02 (3318.4) | 49237.73 (736.8) |
| Gelatin | 22507.43 (3281.6) | 34595.02 (822.9) | 48940.73 (1842.1) |
| 0.01% mTG | 23299.77 (3569.5) | 32816.02 (856.2) | 48458.07 (655.97) |
| 0.02% mTG | 23819.77 (1821.8) | 32794.35 (1609.4) | 43353.07 (1335.69)[a] |
| 0.03% mTG | 25665.10 (198.8) | 33707.02 (2934.2) | 45584.4 (1609.6)[a] |

[a]Indicates significant difference from control (untreated media) ($p < 0.05$) (n = 3)

Table 4 displays no significant difference in cell proliferation levels for each substrate up to a period of 48 hours. After 72 hours however, proliferation levels of cells seeded on 0.02% mTGase-cross-linked gelatin were significantly lower ($p < 0.05$) than the control.

In vitro studies examined independently the cell behaviour when exposed to mTGase and mTGase-cross-linked gelatin. In order to develop a wide ranging toxicity profile of the enzyme, 3T3 fibroblasts were cultured in 6-well tissue culture plates containing 0.05%, 0.005% and 0.0005% mTGase. Cell viability and cell proliferation of 3T3 fibroblasts were quantitatively measured by the trypan blue exclusion and (calorimetric method) AlamarBlue™ assays. After 72 hours cultivation in medium with added mTGase, it was evident from both assays that mTGase at a concentration of 0.05% displayed toxic effects (Table 2 and 3). Lower concentrations of mTGase did not elicit such toxic responses as no statistically significant difference (p<0.05) was noted between the test wells and the control wells (medium and cells). Subsequently, all other tests, including mechanical, were carried out using mTGase concentrations ranging from 0.01% to 0.03%. Concentrations less than 0.01% were deemed to have no effect on the mechanical properties (results not included). The cytocompatibility of gelatin cross-linked with mTGase was examined by similar methods mentioned above, trypan blue exclusion and AlamarBlue™ assay. Although significant differences (p<0.05) were detected in cell viability and cell proliferation between the control substrate (tissue culture grade polystyrene) and gelatin films cross-linked with mTGase, the overall trend discerned in the results of these tests indicate no evidence of toxicity, since cells reached confluency after 72 hours.

Cholecyst-Derived Extracellular Matrix (CEM

Procedure for Isolation Cleaning and Storage

CEM was isolated by a mechanical procedure, cleaned with ethanol and stored in strepto-penicillin. The isolation involved careful peeling of mucosal and serosal layers, and scrapping off the remaining muscularis layer. The isolated CEM was treated with 70% ethanol for 2-4 hrs, for cleaning. Then it was washed thoroughly with distilled water for 24-48 h and preserved in 1% penicillin-streptomycin solution at 4° C.

Procedure for Decellularisation

Decellularisation: Extraction with SDS (32) and trypsin digestion (33) are known for decellularisation of pulmonary heart valves and for producing a novel scaffold from aorta (34).

Procedure: Treat the extracted tissue with 1% Sodium Dodecyl Sulphate (in 10 mM Tris buffer) for 1-4 days. Rinse with Tris Buffer, pH 8 and treat with trypsin-EDTA (0.05% trypsin in 10 mM Tris buffer and 0.1% EDTA, pH 8, overnight (18 h) at 37° C.

Procedure for Cross-Linking

There are several methods of crosslinking: Chemical, Enzymatic and Glycation

Chemical Methods:

Glutaraldehyde treatment—Scaffolds can be immersed in 100 ml of a 0.01M HEPES buffered (pH 7.4) solution containing 0.2 wt % Glutaraldehyde (GA) (from a 25% solution, Merck). The reaction is allowed to proceed for 24 h at 20° C., after which the scaffolds can be stored in a 0.01M HEPES buffered solution containing 0.2 wt % GA.

Carbodiimide treatment: If cross linking is desired, use 20 mM EDC (1-ethy-3-3-dimethylaminoprpyl carbodiimide-HCl) and 10 mM N-hydroxysuccinimide in Hepes buffer, pH 6.5 and the duration of treatment is 72 h at room temperature. Rinse with 100 mM Na2HPO4 to quench and neutralize residual EDC (vanWachem et al 2001).

Ether based: Scaffolds can be immersed in 100 mL of a 2-morpholinoethane sulfonic acid (MES buffer, pH 4.5)]buffered solution containing 4 g of 1,4-butanediol diglycidyl ether (4 wt %). Crosslinking was allowed to proceed for 144 h at 20° C., after which the scaffolds are washed 5 times 30 min with normal saline. The scaffolds can then be stored in 0.01M HEPES containing 20% isopropyl alcohol.

Enzymatic Methods of fixation use transglutaminase or lysyl oxidase.

Cell Studies

Demonstration that the Scaffold is a Non-Toxic Material

The experiment was conducted in a tissue culture laboratory. Two types of cells were used: HeLa cells (epithelial cells) and 3T3 cells (mouse fibroblast like cells). These cells were seeded in 6-well culture plates with routine media (DMEM with streptopencillin). The density of seeding, composition of the culture medium and culture conditions were selected in accordance with routine conditions followed in our research laboratories (NCBES). The scaffold was incubated with the tissue culture system for 4-5 days. The experiment was set up in triplicates. Therefore, at least 15 wells were prepared for each cell type and an equal number of control wells were also set. The control was simply cells seeded on to the culture plates. Everyday, cell-viability (by trypan blue dye exclusion test) was determined in 3 test-wells and 3 control-wells. There was no difference in cell-viability between test and control groups. The test essentially demonstrated the viability of cells when grown along with the scaffold thereby indicating its no-cytotoxic nature.

Demonstration that Cells can Grow on the Scaffold

Scaffolds used for the above cell-viability test were used. After incubation for 4-5 days, the scaffold was fixed in 10% Neutral Buffered Formaldehyde, paraffin blocks were made and routine histology slides were made. The histology slides were examined for light microscopic morphology. Cells were found sticking on the scaffold thereby indicating that cells can grow on the scaffold. Both epithelial cells and 3T3 cells survived on the scaffold surface after 4 days of incubation.

CEM Topography

Figure 24:
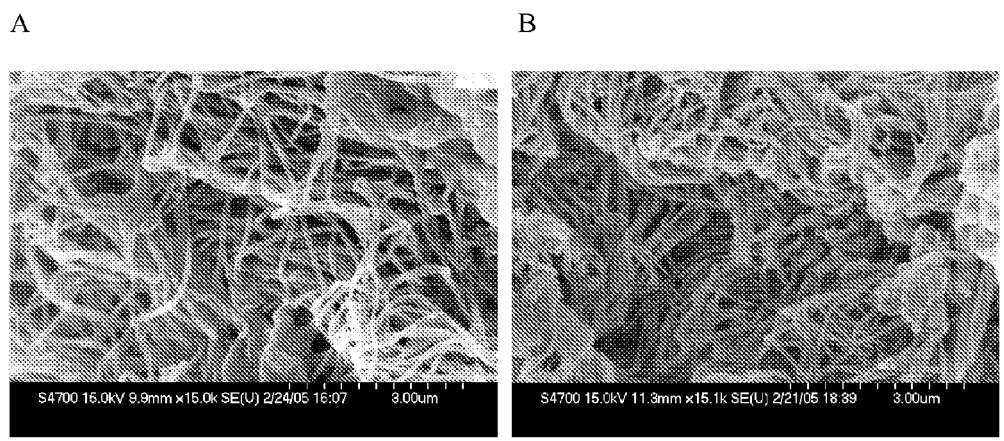
FIG. 24: Scanning electron micrographs of serosal surface (A) and mucosal surface (B) of cholecyst extracellular matrix.

High resolution photomicrographs were captured allowing accurate measurements of the mucosal and serosal surfaces of the CEM (FIG. 24). Mean fiber diameter was 74±4 nm and 80±5 nm on the mucosal and serosal sides respectively and measurements ranged from 29 nm to 155 nm and 37 nm to 219 nm respectively. Mean pore diameter was 216±24 nm and 264±48 nm on the mucosal and serosal sides respectively and measurements ranged from 13 nm to 617 nm and 26 nm to 846 nm respectively. For these two feature types no statistical difference was found between sizes on the serosal and mucosal sides (p<0.05) (Table 5).

TABLE 5

Surface feature measured through scanning electron microscopy photomicrographs, including stereo pairs, on both the mucosal and serosal surfaces of cholecyst-derived extracellular matrix.

|  | Mucosal surface | Serosal surface |
| --- | --- | --- |
| Pore diameter |  |  |
| Mean ± SD (nm) | 216 ± 24 | 264 ± 48 |
| Range (nm) | 13-617 | 26-846 |
| Fiber diameter |  |  |
| Mean ± SD (nm) | 74 ± 4 | 80 ± 5 |
| Range (nm) | 29-155 | 37-219 |
| Elevation height |  |  |
| Mean ± SD (nm) | 316 ± 47 | 295 ± 38 |
| Range (nm) | 67-1003 | 67-902 |

Using stereo pair photomicrographs, a stereoscope and the formula outlined above mean elevation heights calculated on the mucosal and serosal sides of CEM were 316±46 nm and 295±38 nm respectively. Measurements taken ranged from 67 nm to 1003 nm and 902 nm to 67 nm on the mucosal and serosal sides respectively and no statistical difference was found between features on the two sides (p<0.05) (Table 5).

CEM Collagen Fiber Orientation

Figure 25:
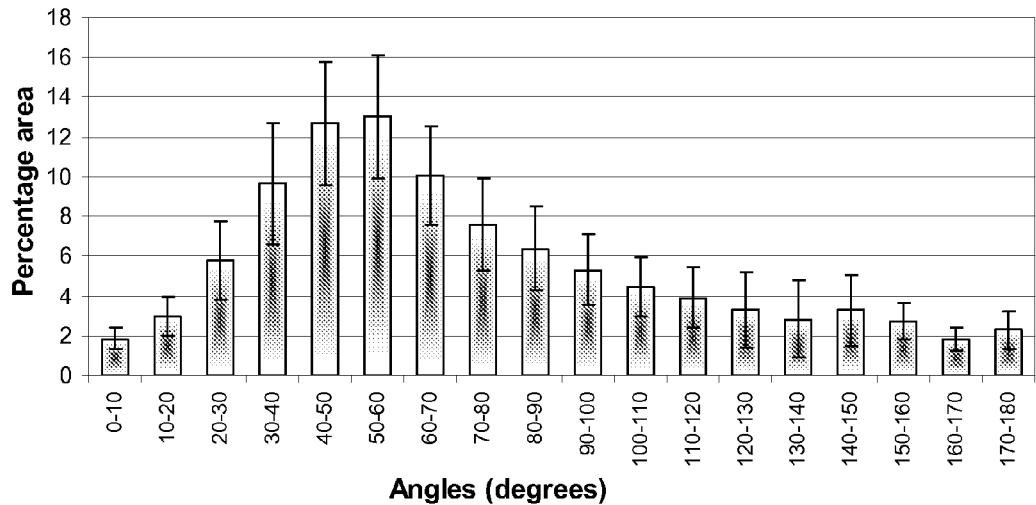
FIG. 25. Collagen fiber orientation per unit area in cholecyst-derived extracellular matrix as measured by polarised light microscopy. Preferred collagen fiber orientation is 55°.
Figure 26:
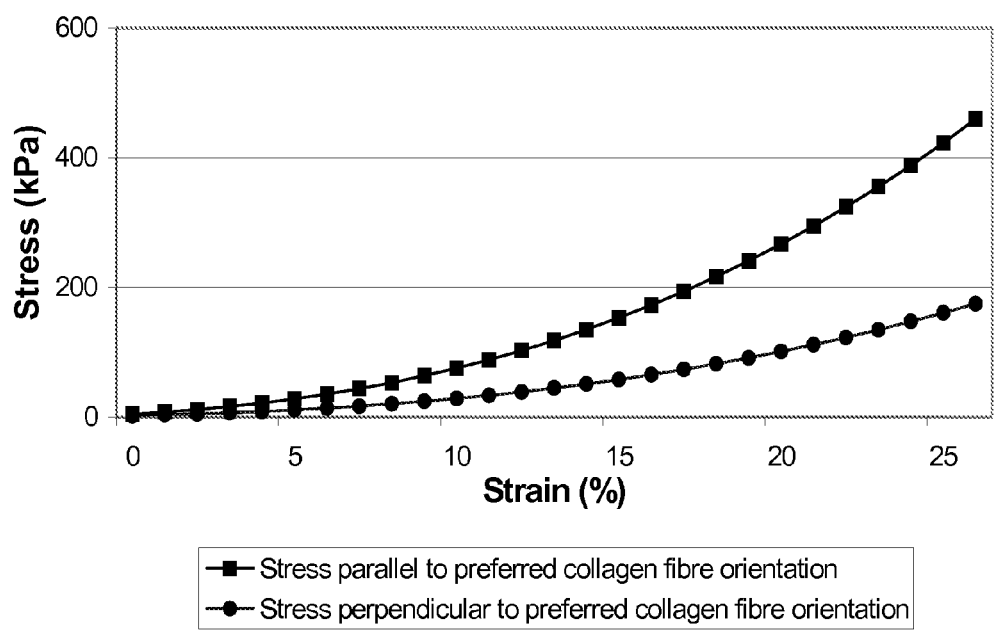
FIG. 26. Stress-strain curve for cholecyst-derived extracellular matrix derived through biaxial mechanical tests. Stiffness is greater in the direction of preferred collagen fiber orientation.
Figure 27:
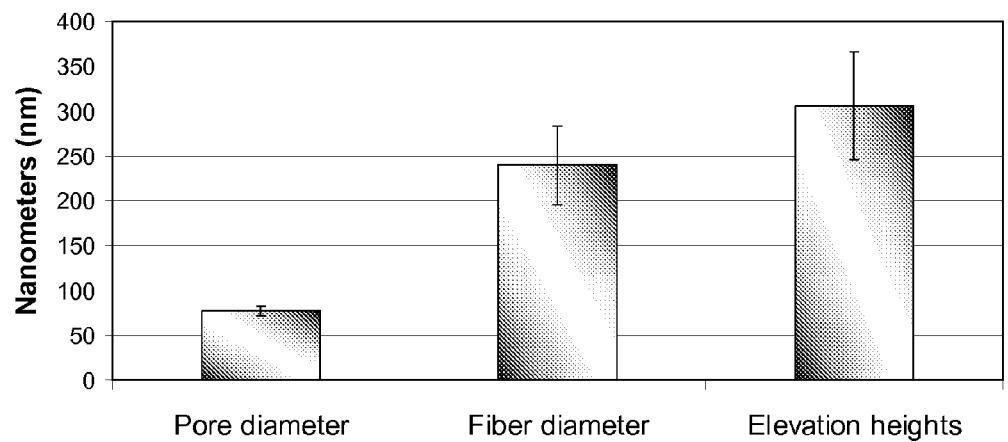
FIG. 27: CEM surface topography measurements.
Figure 28:
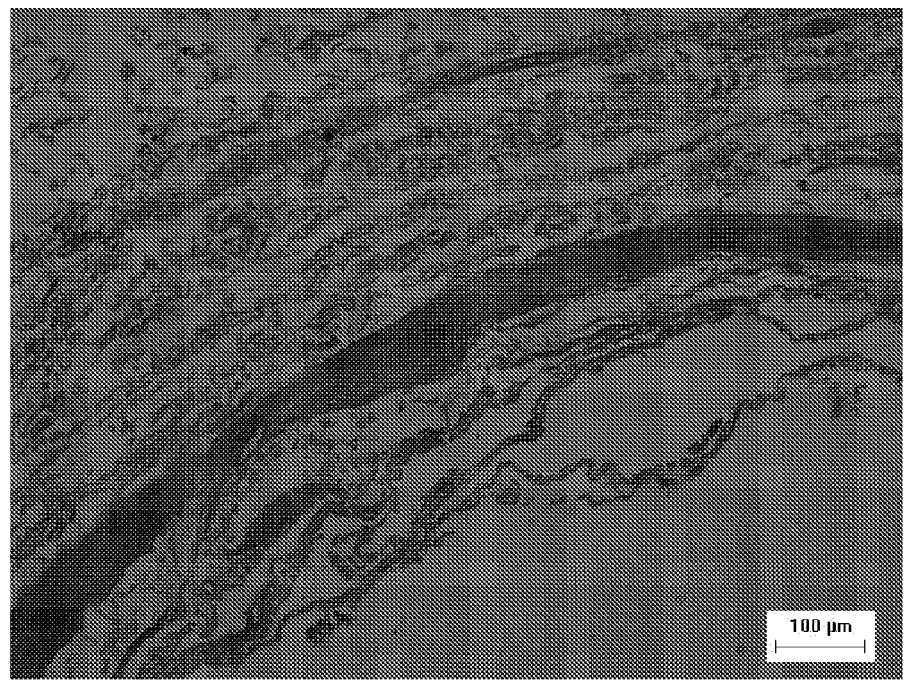
FIG. 28: Picrosirius red stained CEM.

Polarised light microscopy and image analysis techniques were used to generate and analyse photomicrographs thereby elucidating the orientation of collagen fibers in CEM and the preferred collagen fiber orientation. CEM is a thin translucent material thus allowing high quality polarised light microscopy results. Due to the semi-quantitative nature of the technique results were output in terms of percentage area covered with fibers in particular angle ranges. Angle ranges were taken in 10° increments and were all measured relative to the fundus-to-neck axis of the cholecyst. 13% of the area of CEM is covered with collagen fibers oriented between 50° and 60° while only 1.8% of the area is covered with fibers oriented between 160° and 170° (FIG. 25). The preferred collagen fiber orientation was defined as the most frequently occurring orientation of collagen fibers; statistical analysis identified this orientation as 55°. CEM biaxial tests Biaxial tests were preformed along the 55° axis, i.e. parallel to the elucidated preferred collagen fiber ordination and along the 145° axis, perpendicular to collagen fiber orientation. Using Microsoft Excel® (Microsoft Inc., Washington, USA) and Minitab™ (Minitab Inc. Coventry, UK) data generated from the biaxial tests was analysed and a stress-strain curve was created calculating average curves for each sample tested (FIG. 26). Mechanical response of the material was consistent with the fiber architecture; stiffness was higher in the direction of preferred fiber orientation than in the perpendicular direction. The stress-strain curve, in both cases, represented the classic non-linear biological response; low stresses were experienced in the toe region of the curve and beyond a strain of ~10% stiffness of the material increased. Young's modulus of CEM along both axes was measured in the high stiffness region of the stress-strain curves and found to be 1 kPa and 10 kPa in the parallel and perpendicular to the preferred collagen fiber orientation curves respectively.

The CEM samples used in this aspect of the study were isolated from the central region of the cholecyst as it is envisaged that it is from this area that templates for tissue engineering scaffolds could most suitably be created. The techniques used to examine CEM architecture necessitated the fixation of the tissue with glutaraldehyde and, in the case of SEM, the chemical drying of the tissue in HMDS. Effects of glutaraldehyde fixation have been examined using an X-ray microscope to compare the diameter of fixed and unfixed cells; fixation reduced the measurement by only 15%. In another study SEM preparation by ethanol dehydration and HMDS drying was proven to be the most optimal method of maintaining original morphology.

Biologic length scale topographic features have been shown to strongly modulate a variety of fundamental cell behavior in diverse cell types therefore the incorporation of biologic length scale features is a critical parameter in choosing a material for tissue engineering of scaffolds. Recent studies on the response of epithelial cells to a ridge and groove type substratum with pitches ranging from 400 nm-4000 nm indicated that at a pitch of 400 nm cells were aligned and elongated with the ridges, while at a pitch of 4000 nm effects of topography were lost. Also, when cells were exposed to flow, those on the 400 nm pitch surfaces were more tightly adhered than those on the 4000 nm pitch surfaces. In a similar study, further highlighting the importance of topography, and in particular nano-scale topography, the influence of surface elevations ranging from 95-13 nm on the growth of endothelial cells was investigated; the largest cellular response was seen on the 13 nm features. These studies indicate that nanoscale topographical features exert a significant influence on cellular behavior and therefore are a critical factor in the design of scaffolds for tissue engineering applications.

Our findings demonstrate that CEM topography resembles the topographies of previously studied basement membrane layers, which facilitate the growth of cells in vivo; average feature sizes are in the nano-scale range and high standard deviations indicate roughness of both the CEM and basement membrane surfaces. It is therefore concluded that the topography of CEM is conducive to optimal cellular growth and is similar to previously characterised extracellular topographies in vivo.

Previous studies on CEM have demonstrated that it has a low cellular and muscle content and high collagen content. Collagen is an important load bearing structural protein and its structural configuration is therefore intrinsically related to CEM mechanical properties. Polarised light microscopy is a non-destructive technique, which does not necessitate the staining or labelling of tissue samples and has previously been used to identify collagen fiber structural configuration in other biological tissues including bone, cartilage and skin. The system used in this study incorporated circularly polarised light, which eliminated the dependency of brightness on sample orientation, and a rotating polariser which facilitated the capture of 50 views of the same area at different angles thereby allowing the complete visualisation of the crimped collagen fibers. Using a fixed polariser, only sections of the crimped collagen fiber which were not aligned with the transmission axis of either polarising filter would be visible under polarised light.

Although a significant proportion of the area of CEM is covered with fibers oriented between 50° and 60°, studies on small intestinal submucosa (SIS), identified more distinct preferred collagen fiber orientation angle. Collagen fibers in SIS are oriented parallel to the long axis of the intestine with only occasional fiber populations oriented at approximately ±28°. Studies on bovine pericardium, an extensively studied biomaterial have revealed a lesser degree of collagen fiber orientation and substantial inter and intra specimen variability. The more extensive distribution of collagen fiber orientations in CEM and bovine pericardium may be a reflection of the sac-like structure of these organs compared to the tubular structure of the small intestine; however, our findings indicate that, unlike bovine pericardium, CEM does not exhibit similar inter- and intra-sample variability. The consistent, wider range of collagen fiber orientations increases the suitability of CEM as a biomaterial for multi-axial loading applications.

Biaxial, as opposed to uniaxial testing was carried out as it bears more resemblance to potential loading conditions in vivo. All mechanical testing parameters such as preconditioning techniques, maximum loads applied and strain rate were chosen due to their physiological relevance. The gauge length, i.e. the point at which a material transitions from compression to tension, is the point at which strain should ideally be measured from; however due to the folded, wrinkled nature of CEM in the unloaded state and the difficulty associated with balancing the load cells a preload of 10 mN was placed on each load cell prior to commencing the test. The gauge length was measured from the preload. Various clamping mechanisms were considered, however a series of small hooks were chosen as the optimum mechanism as they reduced stress concentrations and permitted stretching of the sample in both directions along the edges.

The stress-strain curve for CEM is typical of that for any soft tissue. The uncrimping of the collagen fibers which are embedded in a compliant extracellular matrix is represented by the low stress toe region of the curve. At a strain of ~10% the response transitions from low stress to high stress and the material becomes considerably stiffer possibly due to a combination of fully extended collagen fibers and collagen fiber re-alignment as occurs in other soft tissues. CEM displays a more elastic response than that of SIS. At a biaxial stress of 250 kPa CEM exhibits strains of 23.4% and 30.5% parallel to and perpendicular to the preferred collagen orientations respectively, while at the same level of stress SIS strains by only 8% along each axis. This difference in strain responses may be attributed to a more distinct collagen fiber orientation in SIS compared to that of CEM, different sample mounting techniques and considerable differences in thickness between the two materials; fresh SIS has a thickness of 1 mm compared to 0.35 mm for SIS.

The wide distribution of collagen fiber orientation angles in CEM is also reflected by the differences in the mechanical responses of the axes parallel to and perpendicular to the preferred fiber orientation. Previous studies have shown that heart valves have a particularly distinct collagen fiber orientation and exhibit a high degree of anisotropy (18, 30); at 60N/m of tension there is a difference of 65% strain between the responses of the circumferential and radial axes of a heart valve cusp. At the same level of tension CEM exhibits only an 8% difference.

Further, more detailed mechanical testing of CEM, possible involving strain field analysis or investigating the possibility of layering the material may reveal more conservative levels of strain and a sharper transition from the low stress region to the high stress region. However, biaxial mechanical test findings in this study have confirmed that stiffness is higher in the preferred collagen fiber direction, i.e. 55° to the fundus-to-neck axis, than in that of the perpendicular direction and that the degree of anisotropy is reflected in the differences in strains between the parallel and perpendicular stress-strain curves.

CEM is an anisotropic biomaterial with similar topographic features to surfaces which have previously been demonstrated to support the growth of cells. Findings of this study also indicate that CEM has a preferred orientation of 55°, which is an important factor when isolating tissue engineering scaffold templates. Additionally, biaxial tests have confirmed the findings of the collagen orientation study and highlighted the intrinsic relationship between collagen fiber orientation and mechanical properties. Architectural characteristics of a material play a signficant role in determining potential applications for the material and are critical parameters for tissue engineering scaffold design. These results demonstrate the suitability of using CEM as a tissue engineering scaffold material.

Susceptibility of CEM-Based Scaffolds to in vitro Collagenase Degradation

The CEM was isolated by mechanically peeling off the mucosal and serosal layers of the cholecyst. The isolated CEM or crosslinked CEM (treated with 0.625% glutaraldehyde (GA)) was either freeze-dried (CEMfd, GAxCEMfd) or vacuum-dried (CEMvd, GAxCEMvd).

In vitro collagenase degradation studies were performed on 3 mg of samples in 1 ml of Tris-HCl buffer(pH 7.4) containing 30 u/ml of bacterial collagenase, 0.005M CaCl, and 0.05 mg/ml sodium azide at 37° C. The degradations were stopped at 2, 4, 24, 48 and 72 hours. CEMvd and CEMfd samples showed a maximum percent weight loss of 72.19±2.08 and 79.53±2.42 respectively, while GAxCEMvd and GAxCEMfd showed just 2.96±0.69 and 3.94±1.44. These results indicate that crosslinking CEM with GA drastically reduced its collagenase degradability ($p<0.005$). The method of drying did not show significant effect on the rate of collagenase degradation of the CEM and GAxCEM samples, except for CEM at 2 h ($p<0.05$).

Collagen is the major structural component (>70%) of the cholecyst-derived extracellular matrix. The present invention reveals that its susceptibility to collagenase degradation can be reduced by crosslinking with glutaraldehyde.

Evaluation of in vitro swelling and degradation behaviour of cholecyst derived extracellular matrix (CEM) and in vivo tissue response elicited by CEM in subcutaneous rat implant model Methods: CEM was isolated by carefully peeling/scraping off the mucosal and serosal layers of the cholecyst. The samples were vacuum/freeze dried. Some were crosslinked with 0.625% glutaraldehyde (GA). Swelling and degradation studies were carried out in distilled water and phosphate buffer (pH7.4). 1×1 $cm^2$ CEM, GA crosslinked CEM and porcine heart valves were immobilized on subcutaneous tissue with non degradable prolene suture. Rats were sacrificed at 21 and 63 days to study the tissue response to CEM based implants.

Figure 30:
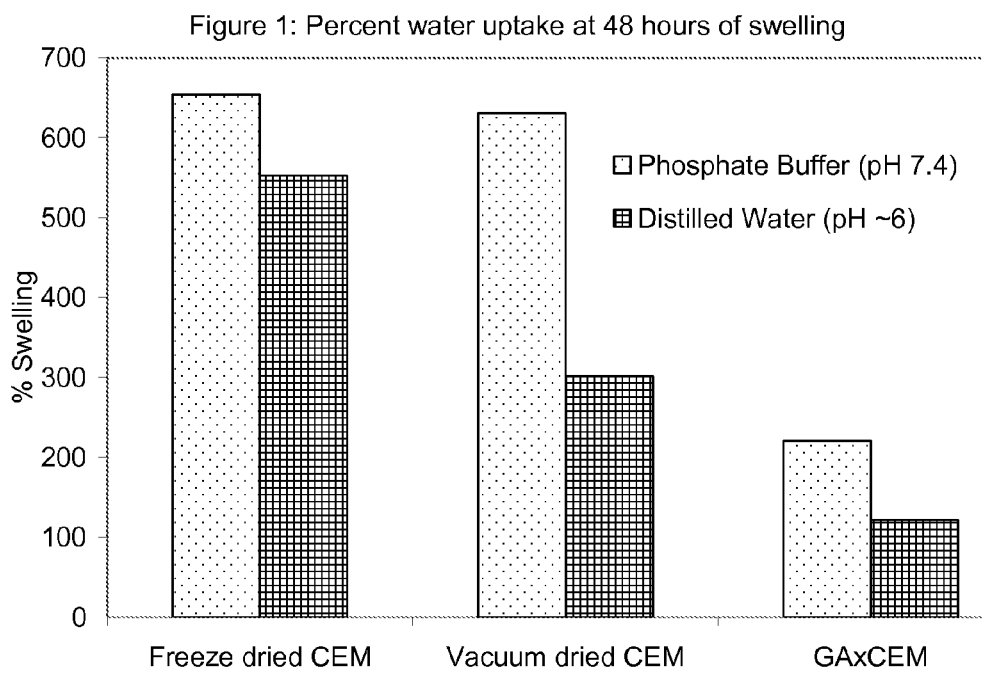
FIG. 30. % water uptake after 48 hours of swelling.
Figure 31:
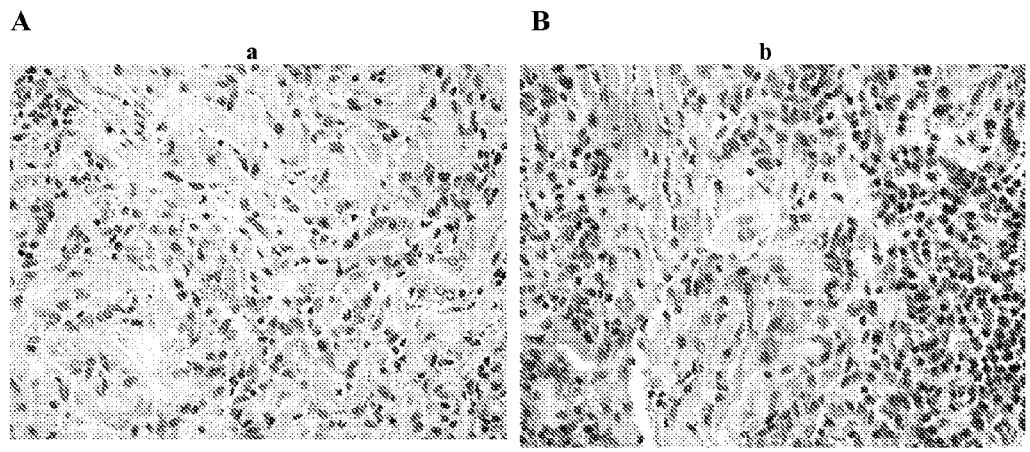
FIG. 31: Hematoxylin & Eosin stained section (x400) of tissue response elicited by a) cholecyst derived extracellular matrix (CEM) and b) CEM crosslinked with 0.625% glutaraldehyde, at 21 days.

Results: Freeze dried samples showed higher degree of water uptake than vacuum dried samples. GA crosslinking drastically reduced the amount of water uptake (FIG. 30). Fickian diffusion was observed with all the samples ($n=0.23±0.07$). Loss of weight was observed within 24 hours in case of vacuum/freeze dried CEM samples. The subcutaneously implanted samples showed integration with the extracellular matrix and native CEM samples were completely absorbed by host tissue by 63 days. The number of inflammatory cells infiltrating the implant sited was higher in GA crosslinked samples, with minimal foreign body giant cell response (FIG. 31a&b).

Crosslinking is essential to prevent lose of bioactive components from the ECM. Native CEM samples showed better tissue compatibility. CEM has good potential for tissue engineering and other implant applications.

Burst Strength

Figure 29:
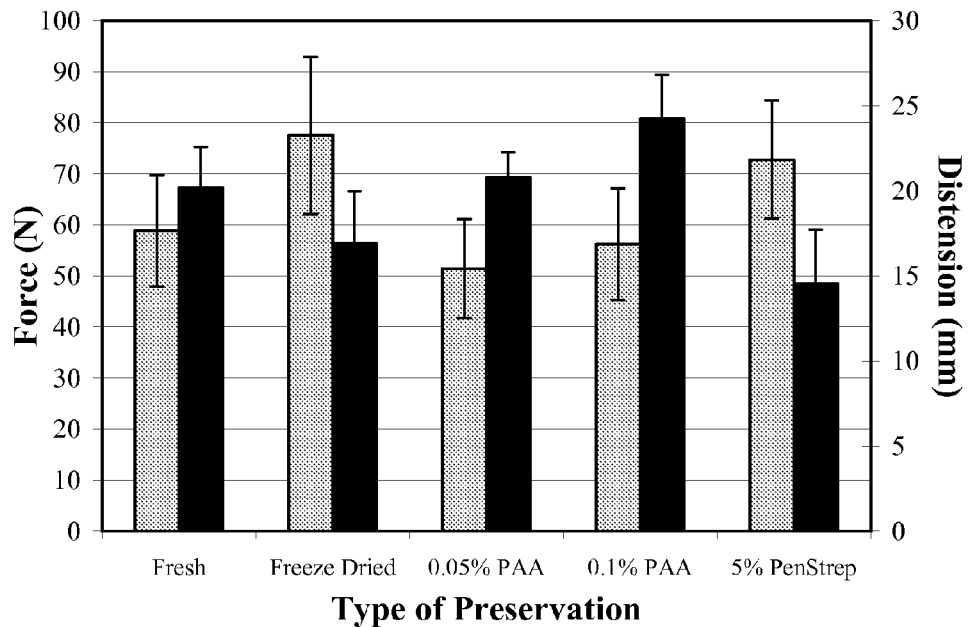
FIG. 29: Burst force required to rupture CEM (grey) and amount of distension (black) for various preservation methods.

The burst strength and distension of preserved tissue was measured and the primary material axis was found. CEM scaffolds were isolated from fresh tissue by mechanically separating the acellular layer from the inner mucosa and outer serosa. A ball burst test jig was fabricated to comply with ASTM (43) standards. Samples were either tested immediately, or after preservation for one week (n=5 in all cases). Bursting force, distension to burst and thickness were recorded. Results were compared by ANOVA ($p<0.05$). In one example, five CEM scaffolds mounted on a uniform elastic ring embedded with hooks every 15°. These preparations were tested according the method of Choi et al. (44) with an precision of ±7.5°. The average thickness of the CEM was 0.15±0.06 mm. Compared to fresh tissue, no preservation method significantly changed the mechanical strength over one week. A 5% solution of penicillin and streptomycin, did however, stiffen the matrix (FIG. 29). A principle material axis was oriented 60°±22.5° from the long axis. The matrix did not show a large bias in any direction and this may have increased deviation. Comparing burst test results from the single-layer CEM to dual-layer small intestinal submucosa (SIS) and urinary bladder submucosa (UBS) (44), showed no significant differences in the burst strength. These data show that single-layer CEM scaffolds exhibit high extensibility and similar strength to dual-layer scaffolds.

In the following example, the burst strength and stiffness of fresh tissue samples were measured using a ball burst test jig. Four cholecyst derived extracellular matrices (CEM) were isolated from fresh tissue by mechanically separating the mostly acellular layer from the inner mucosa and outer muscularis. Each layer was slowly peeled from the one below using forceps to limit the amount of mechanical damage to the collagen scaffold through extraction. Specimens were placed into a phosphate buffered saline (PBS) solution to prevent dehydration between the time of isolation and testing, no more than 3 hours. The burst jig was fabricated to comply with the ASTM D3787-01, using a 44.45 mm inner diameter ring to clamp the specimen and a 25.4 mm diameter ball to apply the load perpendicular to the tissue orientation with an Instron (Instron Corp. Canton, Mass.) load frame. The plunger moved at a constant speed of 5 mm/s for the duration of the test. Bursting force, distension to burst, thickness, and stiffness were recorded. The average thickness of the acellular CEM was 0.15 mm±0.06 mm, approximately half of the unprocessed thickness of 0.4 mm±0.04 mm. Both discarded layers This multiaxial test allows a more realistic representation of tissue performance, shown below, in a pressurised space such as the thoracic or abdominal cavities than does uniaxial testing.

| Disten. (mm) | Burst Strength (N) | Stiffness (N/m) |
| --- | --- | --- |
| 20.2 ± 2.4 | 58.8 ± 11.0 | 2962.2 ± 767.7 |

Figure 32:
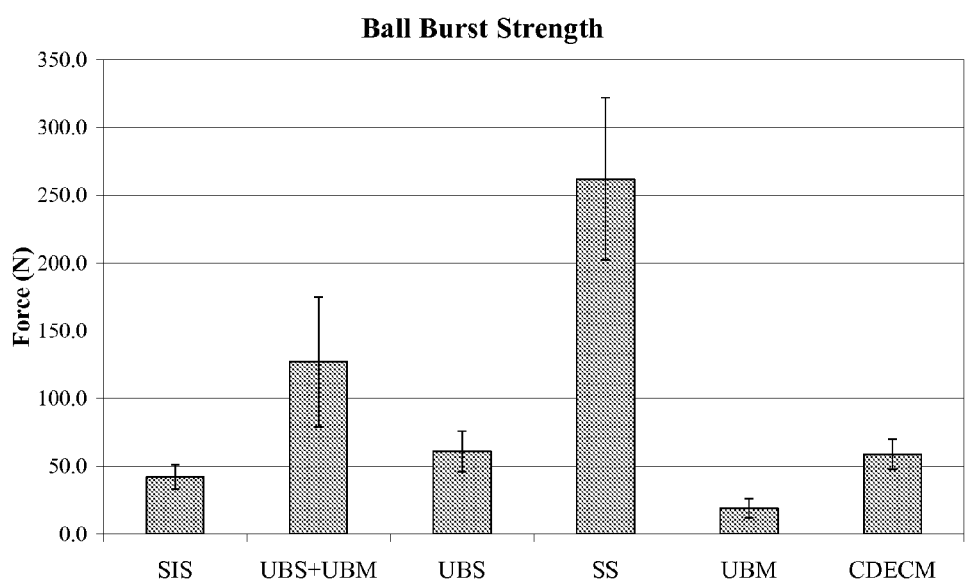
FIG. 32—Comparison of ball burst strengths of several, double layer acellular matrices as obtained by Freytes et al. (42) and the new CDECM, tested as a single layer. Means±1 SD are shown.

Other acellular matrices, studied by several institutions have been subjected to ball burst testing and the results are comparable to those obtained with the CEM. (FIG. 32) The CEM can be layered to customize these properties for a desired application. Current tissue engineered scaffolds are used for a variety of conditions and treatments. None of the material properties are customised, however, to any of those treatments. Made of mostly acellular material, the tissue substrate provided by the present invention requires minimal decullarisation, maintaining the in vivo structural integrity and natural growth factors to facilitate host tissue repair.

REFERENCES

1. Anilkumar T, Biggs M, Pandit A. Cholecyst-derived Extracellular Matrix: A Potential Scaffold. In: European Society for Biomaterials Conference; 2005 11-15, Sep. 2005; Sorento, Italy; 2005.
2. Curtis A S, Varde M. Control of Cell Behavior: Topological Factors. J Natl Cancer Inst 1964;33:15-26
3. Den Braber E T, De Ruijter J E, Smits H T, Ginsel L A, von Recum A F, Jansen J A. Effect of parallel surface microgrooves and surface energy on cell growth. J Biomed Mater Res 1995;29(4):511-8.
4. Den Braber E T, De Ruijter J E, Smits H T, Ginsel L A, von Recum A F, Jansen J A. Quantitative analysis of cell proliferation and orientation on substrata with uniform parallel surface micro-grooves. Biomaterials 1996;17(11):1093-9.
5. Dalby M J, Childs S, Riehle M O, Johnstone H J, Affrossman S, Curtis A S. Fibroblast reaction to island topography: changes in cytoskeleton and morphology with time. Biomaterials 2003;24(6):927-35.
6. Evans M D, Dalton B A, Steele J G. Persistent adhesion of epithelial tissue is sensitive to polymer topography. J Biomed Mater Res 1999;46(4):485-93.
7. Meyle J, Gultig K, Nisch W. Variation in contact guidance by human cells on a microstructured surface. J Biomed Mater Res 1995;29(1):81-8.
8. Barbucci R, Lamponi S, Magnani A, Pasqui D. Micropatterned surfaces for the control of endothelial cell behaviour. Biomol Eng 2002; 19(2-6): 161-70.
9. Peters K, Unger R E Kirkpatrick C J, Gatti A M, Monari E. Effects of nano-scaled particles on endothelial cell function in vitro: studies on viability, proliferation and inflammation. J Mater Sci Mater Med 2004;15(4):321-5.
10. Teixeira A I, Abrams G A, Bertics P J, Murphy C J, Nealey P F. Epithelial contact guidance on well-defined micro- and nanostructured substrates. J. Cell Sci 2003:116(Pt 10):1881-92.
11. Flemming R G, Murphy C J, Abrams G A, Goodman S L, Nealey P F. Effects of synthetic micro- and nano-structured surfaces on cell behavior. Biomaterials 1999;20(6):573-88.
12. Chung T W, Liu D Z, Wang S Y, Wang S S. Enhancement of the growth of human endothelial cells by surface roughness at nanometer scale. Biomaterials 2003;24(25):4655-61.
13. Dalby M J, Riehle M O, Johnstone H, Affrossman S, Curtis A S. In vitro reaction of endothelial cells to polymer demixed nanotopography. Biomaterials 2002;23(14):2945-54.
14. Kauri N W, Liliensiek S, Teixeira A I, Abrams G, Campbell S, Nealey P F, et al. Biological length scale topography enhances cell-substratum adhesion of human corneal epithelial cells. J Cell Sci 2004;l 17(Pt 15):3153-64.
15. Murphy C J, Nealey P F, Campbell S F. Substratum topography modulates proliferation of cornel epithelial cells. In: The Association for Research in Vision and Ophthalmology 2004 Annual Meeting; 2004; Florida, USA; 2004.
16. Fung Y C. Biomechanics Mechanical Properties of Living Tissues. $2^{nd}$ ed. New York: Springer-Verlag; 1993.
17. Gloeckner D C, Sacks M S, Billiar K L, Bachrach N. Mechanical evaluation and design of a multilayered collagenous repair biomaterial. J Biomed Mater Res 2000;52(2):365-73.
18. Brody S, Pandit A. Microarchitectural Characterization of the Aortic Heart Valve. In: Hasirci N, Hasirci V, editors. Biomaterials: from molecules to engineered tissues. Ney York: Kluwer Academic/Plenum; 2004.p. 167-86.
19. Jearanaikoon S, Abraham-Peskir J V. An X-ray microscopy perspective on the effect of glutaraldehyde fixation on cells. J Microsc 2005;218(Pt 2):185-92.
20. Fratesi S E, Lynch F L, Kirkland B L, Brown L R. Effects of SEM preparation techniques on the appearance of bacteria and biofilms in the carter sandstone. Journal of Sedimentary Research 2004;74(6):858-867.
21. Brody S, Anilkumar T, Liliensiek S, Last J A, Murphy C J, Pandit A. Characterising Nanoscale Topography of the Aortic Heart Valve Basement Membrane for Tissue Engineering Scaffold Design. Tissue Engineering 2005;Accepted.
22. Abrams G A, Schaus S S, Goodman S L, Nealey P F, Murphy C J. Nanoscale topography of the corneal epithelial basement membrane and Descemet's membrane of the human. Cornea 2000;19(1):57-64.
23. Arokoski J P, Hyttinen M M, Lapvetelainen T, Takacs P, Kosztaczky B, Modis L, et al. Decreased birefringence of the superficial zone collagen network in the canine knee (stifle) articular cartilage after long distance running training, detected by quantitative polarized light microscopy. Ann Rheum Dis 1996;55(4):253-64.
24. Jacques S L, Roman J R, Lee K. Imaging superficial tissues with polarized light. LasersSurg Med 2000;26(2): 119-29.
25. Bigi A, Cacchioli A, Fichera A M, Gabbi C, Koch M H, Ragionieri L, et al. X-ray diffraction and polarizing optical microscopy investigation of the structural organization of rabbit tibia. J Biomed Mater Res 1998;41(2):289-95.

26. Sacks M S, Gloeckner D C. Quantification of the fiber architecture and biaxial mechanical behavior of porcine intestinal submucosa. J Biomed Mater Res 1999;46(1):1-10.
27. Hiester E D, Sacks M S. Optimal bovine pericardial tissue selection sites. I Fiber architecture and tissue thickness measurements. J Biomed Mater Res 1998;39(2):207-14.
28. Christie G W, Barratt-Boyes B G. Biaxial mechanical properties of explanted aortic allograft leaflets. Ann Thorac Surg 1995;60:160-4.
29. Thubrikar M J. The Aortic Valve. Florida: CRC press; 1990.
30. Billiar K L, Sacks M S. Biaxial mechanical properties of the natural and glutaraldehyde treated aortic valve cust-Part I: Experimental results. J Biomech Eng 2000;122(1): 23-30.
31. Christie G W, Barratt-Boyes B G. Mechanical properties of porcine pulmonary valve leaflets: How do they differ from aortic valve leaflets? Ann Thorac Surg 1995;60: 195-9.
32. Booth C, Korossis S A, Wilcox H E, Watterson K G, Kearney J N, Fisher J, Ingham E. Tissue engineering of cardiac valve prosthesis I: development and histological characterization of an acellular porcine scaffold. J Heart valve Dis 2002; 11 (4): 457-462.
33. Steinhoff G, Stock U, karim N, Mertsching H, Timke A, meliss R R, Pethig K, Haverich A, Bader A. Tissue Engineering of pulmonary heart valve on allogenic acellular matrix conduits: in vivo restoration of valve tissue. Circulation 2000: 102 (19-III); 50-55.
34. Lu Q, ganesan K, Simionescu D T, Vyavahare N R (2004). Novel porus aortic elastin and collagen scaffolds for tissue engineering. Biomaterials 25: 5227-5237.
35. vanWachem P B, Plantinga J A, Wissink M J, Beemink R, Poot A A, Engbers G H, Beugeling T, van Aken W G (2001). In vivo biocompatibility of carbodiimide-cross linked collagen matrices: effects of cross link density, heparin immobilization and bFGF loading, J Biomed mater Res 55(3) 368-378.
36. Ikura K, Kometani T, Sasaki, R, Chiba H. Crosslinking of Soybean 7S and 11S Protein by Transglutaminase. Agricult Biol Chem 1980;44:2979-2984.
37. Motoki M, Nio N. Crosslinking Between Different Food Proteins by Transglutaminase. J Food Sci 1983;48:561-566.
38. Kurth L, Rogers P J. Transglutaminase Catalysed Crosslinking of Myosin to Soya Protein, Casein and Gluten. J Food Sci 1984;49:573-589.
39. Ando H, Adachi M, Umeda K, Matsurra A, Nonaka M, Uchio R, Tanaka H, Motoki M. Purification and characteristics of a novel transglutaminase derived from microorganisms. Agricult Biol Chem 1989;53:2613-2617.
40. Gu Y S, Matsumura Y, Yamaguchi S, Mori T. Action of protein-glutaminase on alpha-lactalbumin in the native and molten globule states. J Agricult Food Chem 2001;49: 5999-6005.
41. Kang Y N, Kim H, Shin W S, Woo G, Moon T W. Effect of disulfide bond reduction on bovine serum albumin-stabilized emulsion gel formed by microbial transglutaminase. J Food Sci 2003;68:2215-2220.
42. D. O. Freytes et al. Biomaterials 25 (2004) 2353-2361.
43. ASTM standards source [CD] 2004.
44. Choi et al. J Biomech Eng. 112 (1990)

The invention claimed is:

1. A tissue scaffold comprising a sterilized, cross-linked, decellularized and isolated layer or layers of extra cellular matrix tissue obtained from a cholecyst.

2. The tissue scaffold as claimed in claim 1, wherein the cholecyst is of porcine or mammalian origin.

3. The tissue scaffold as claimed in claim 1, wherein the cross-linking is achieved by a method selected from the group consisting of formaldehyde cross-linking, glutaraldehyde cross-linking, enzymatic cross-linking, glycation, dialdehyde starch cross-linking, glyceraldehyde cross-linking, cyanamide cross-linking, diimide cross-linking, diisocyanate cross-linking, dimethyl adipimidate cross-linking, carbodiimide cross-linking, cross-linking with an epoxy compound, and genepin cross-linking.

4. The tissue scaffold as claimed in claim 1, wherein the tissue has been cross-linked using 20 mM EDC (1-ethyl-3-3-dimethylaminopropyl carbodiimide-HCl) and 10 mM N-hydroxysuccinimide in Hepes buffer, pH 6.5.

5. The tissue scaffold as claimed in claim 1, wherein the tissue scaffold is formed as a mechanical composite by alternate stacking of the extra cellular matrix tissue layers on top of each other.

6. The tissue scaffold as claimed in claim 1, wherein the tissue is sterilized by a method selected from antibiotic treatment, treatment with peracetic acid or weak acid or alkali, gamma irradiation, or treatment with 60-80% alcohol.

7. The tissue scaffold as claimed in claim 1, wherein the tissue scaffold is stored for use in peracetic acid, gluteraldehyde solution, antimicrobial solution, or frozen, air dried or irradiated for storage, or stored in an air-tight container.

8. The tissue scaffold as claimed in claim 1, wherein the cholecyst is porcine cholecyst.

9. The tissue scaffold as claimed in claim 1, wherein the tissue scaffold is in the form of a sheet, a cylindrical tube, a dome, or a fundus.

* * * * *